United States Patent [19]

Desai et al.

[11] Patent Number: 5,958,792
[45] Date of Patent: Sep. 28, 1999

[54] COMBINATORIAL LIBRARIES OF SUBSTRATE-BOUND CYCLIC ORGANIC COMPOUNDS

[75] Inventors: Manoi C. Desai, Pleasant Hill; John M. Nuss, Danville; Kerry L. Spear, Oakland; Rajinder Singh, Walnut Creek; Paul A. Renhowe, Danville; Edward G. Brown, Lafayette; Lutz Richter, Pacifica, all of Calif.; Barbara O. Scott, San Antonio, Tex.

[73] Assignee: Chiron Corporation, Emeryville, Calif.

[21] Appl. No.: 08/485,006

[22] Filed: Jun. 7, 1995

[51] Int. Cl.[6] .................... G01N 33/543; G01N 33/545; G01N 33/53; A61K 38/06
[52] U.S. Cl. .................. 436/518; 436/531; 530/330; 530/333; 530/334; 435/7.1
[58] Field of Search .................. 530/334, 330, 530/333, 335; 435/7.1; 436/518, 531

[56] References Cited

U.S. PATENT DOCUMENTS

| | | |
|---|---|---|
| 3,634,364 | 1/1972 | Greenbelt et al. . |
| 4,833,092 | 5/1989 | Geysen ................................ 436/501 |
| 5,010,175 | 4/1991 | Rutter et al. ........................ 530/334 |
| 5,066,716 | 11/1991 | Robey et al. ....................... 525/54.1 |
| 5,143,854 | 9/1992 | Pirrung et al. ..................... 530/334 |
| 5,182,366 | 1/1993 | Huebner et al. ................... 530/334 |
| 5,194,392 | 3/1993 | Geysen ................................ 436/518 |
| 5,225,533 | 7/1993 | Rutter et al. ........................ 530/334 |
| 5,252,296 | 10/1993 | Zuckermann et al. .............. 422/116 |
| 5,266,684 | 11/1993 | Rutter et al. ........................ 530/334 |
| 5,288,514 | 2/1994 | Ellman .................................. 435/4 |

FOREIGN PATENT DOCUMENTS

| | | |
|---|---|---|
| 24 47 305 | 4/1975 | Germany . |
| 1037474 | 7/1966 | WIPO . |
| WO86/00991 | 2/1986 | WIPO . |
| WO86/06487 | 11/1986 | WIPO . |
| WO90/09395 | 8/1990 | WIPO . |
| WO91/17823 | 11/1991 | WIPO . |

OTHER PUBLICATIONS

Simon, Reyna et al., " Peptoids: A Modular Approach to Drug Discovery" *Proc. Nat.l Acad. Sci. USA* (1992) vol. 89:9367–9371.

Zuckerman, Ronald et al., " Efficient Method for the Preparation of Peptoids [Oligo(N–substituted glycines)] by Submonomer Solid–Phase Synthesis", *Chemtracts–Macromolecular Chemistry* (1993) vol.4:80–83.

Marcincin, Anton et al., "Studium Adheznych Vlastnosti N–Substituovanych Polyamidov.ll. Adhezna Praca N–Alkoxymetyl–Poly–Kaprolaktamu Kniektorym Polymerom", *Plasty Kauc* (1975) vol.12:101–104.

Kasica, H. et al., " Electrical Conductivity of N–Substituted Polyamides", *Journal of Polymer Science Part A–1* vol.6:1615–1623.

Cosani A. et al., " N–Substituted Poly ( –amino acids). 1. Synthesis and Characterization of Poly (N–methyl–y–mehtyl L–Glutamate) and Poly ( N–methyl–Y–ethyl L–glutamate) [1] ", *Macromolecules* (1978) vol.11 No.5;1041–1045.

Bunin, Barry A. and Ellman Jonathan A., "A General and Expedient Method for the Solid–Phase Synthesis of 1,4–Benzodiazephine Derivatives", *J.Am.Chem.Soc.* (Oct. 1992) vol.114:10997–10998.

Bunin, Barry A. et al., "The Combinatorial Synthesis and Chemical and Biological Evaluation of a 1,4–Benzodiazephine Library", *Proc.Natl.Acad.Sci. USA* (May. 1994) vol.91:4708–4712.

Chen, Chixu, et al., "'Analogous' Organic Synthesis of Small–Compound Libraries: Validation of Combinatorial Chemistry in Small–Molecule Synthesis," *J. Am. Chem. Soc.*, (1994) vol. 116, pp. 2661–2662.

Deshpande, Milind S., "Formation of Carbon–Carbon Bond on Solid Support: Application of the Stille Reaction", *Tetrahedron Lett.* (1994) vol.35, No.31:5613–5614.

Dower W.J. and Fodor, S.P.A., "Chapter 28. The Search for Molecular Diversity (II): Recombinant and Synthetic Randomized Peptide Libraries", *Annu.Rep.Med.Chem.* (1991) vol.26:271–280.

Furka, A., et al. "General Method for Rapid Synthesis of Multicomponent Peptide Mixtures", *Int.J.Peptides Protein Res.* (1991) vol.37:487–493.

Furka, A., et al., "Cornucopia of Peptides by Synthesis", Dept. Org. Chem, Univ. Budapest, Hungary. [Note: This is the best copy available].

Hobbs–DeWitt, Sheila, et al., "'Diversomers': An Approach to Nonpeptide, Nonoligomeric Chemical Diversity", *Proc. Natl.Acad.Sci. USA* (Aug. 1993) vol.90:6909–6913.

(List continued on next page.)

*Primary Examiner*—Ponnathapura Achutamurthy
*Assistant Examiner*—P. Ponnaluri
*Attorney, Agent, or Firm*—Bozicevic, Field & Francis; Kenneth M. Goldman; Robert P. Blackburn

[57] ABSTRACT

The invention relates to libraries of cyclic organic compounds and method of producing and assaying such libraries. According to the invention, each cyclic organic compound is constructed from a starting material in the form of a solid surface derivatized with a starting resin. Compounds are reacted with the resin to add or to form a cyclic group. The reactions are preferable carried out using a split resin procedure so that different compounds can be reacted with a plurality of subamounts so as to increase the size of the library. For example, compounds are reacted with a solid support bound starting resin to obtain a compound which includes an aldehyde functional group wherein the aldehyde compound or compounds reacted with it have substituents which are varied such that a mixture of products is obtained. The invention further relates to methods of producing combinatorial libraries of cyclic organic compounds from substrate bound compounds by cleaving the compounds from the support after synthesizing is completed and to assaying libraries of such compounds.

14 Claims, 1 Drawing Sheet

OTHER PUBLICATIONS

Houghten et al., "Generation and Use of Synthetic Peptide Combinational Libraries for Basic Research and Drug Discovery", *Nature* (1991) vol.354:84–86.

Kates S.A. et al., "Automated Allyl Cleavage for Continuous–Flow Synthesis of Cyclic and Branched Peptides" *Anal. Biochem.* (1993) vol.212:303–310.

Robey et al., "Automated Synthesis of N–Bromoacetyl–Modified Peptides for the Preparation of Synthetic Peptide Polymers, Peptide–Protein Conjugates, and Cyclic Peptides", *Analytical Biochemistry* (1989) vol.177:373–377.

Robey, F.A. et al. "Synthesis, Analyses and Uses of Site–Specific Bromoacetyl–Derivatized Synthetic Peptides: Starting Materials for Countless New Cyclic Peptides, Peptomers and Peptide Conjugates", *Chimica Oggi* (1992) 27–31.

Stewart, J.M. and Young, J.D., "Solid Phase Peptide Synthesis", (2nd ed.), Pierce, Rockford, Il (1984) 30–31.

Zuckermann, R.N. et al., "Design Construction and Application of Fully Automated Equimolar Peptide Mixture Synthesizer", *Intl.J.Peptide Protein Res.*, (1992) vol.40:497–506.

Desai et al. Drug development and Research., vol. 33., pp. 174–188., 1994.

Gordon et al ., Journal of Medicinal Chemistry., vol. 37., No. 10. May 13, 1994.

Zuckermann et al., J. Am. Chem. Soc., vol. 114., pp. 10646–10647., 1992.

COMBINATORIAL LIBRARIES OF SUBSTRATE-BOUND CYCLIC ORGANIC COMPOUNDS

This application is related to an U.S. application Ser. No. 08/487,282, entitled "SYNTHESIS OF N-SUBSTITUTED OLIGOMERS", filed on Jun. 7, 1995, which is assigned to the same assignee as the present application. The application 08/487,282 is a continuation-in-part of earlier filed U.S. application Ser. No. 08/277,228, filed Jul. 18, 1994, now abandoned, which application is a continuation-in-part of earlier filed U.S. patent application Ser. No. 08/126,539, filed Sep. 24, 1993, now abandoned, which application is a continuation-in-part of earlier filed U.S. patent application Ser. No. 07/950,853, filed Sep. 24, 1992, now abandoned, all of which applications are commonly assigned and which applications are incorporated herein by reference in their entirety.

FIELD OF THE INVENTION

This present invention relates generally to chemical synthesis technologies. More particularly, the present invention relates to the synthesis of combinatorial libraries of heterocyclic organic compounds synthesized on solid phase starting materials and to methods of assaying such libraries for biological activity.

BACKGROUND OF THE INVENTION

Standard methods analogous to classical solid-phase methods for peptide synthesis could be applied to synthesize libraries of peptides and peptide-like compounds. In accordance with such methods, the carboxylate of N,α-Fmoc-protected (and side-chain protected) amino acids may be activated and then coupled to a resin-bound amino group. The Fmoc group is then removed followed by addition of the next monomer. Such an approach is not desirable due to the time and cost of preparing suitable quantities of a diverse set of protected N-substituted amino acid monomers. Adding and removing the Fmoc or other protective groups is time consuming and inefficient.

One approach to the discovery of new pharmaceutically active organic drugs (i.e., compounds with the 3-D structure needed for binding) relies primarily on X-ray crystallography of purified receptors: once the binding site is identified, organic molecules are designed to fit the available steric space and charge distribution. However, it is often difficult to obtain purified receptors, and still more difficult to crystallize the receptor so that X-ray crystallography may be applied. It is also nontrivial to devise an appropriate ligand, even after the binding site has been properly identified. Overall, it is extremely difficult to design useful pharmaceutically active compounds due to a number of factors such as the difficulty in identifying receptors, purifying and identifying the structures of compounds which bind to those receptors and thereafter synthesizing those compounds.

Another approach to the discovery of new drugs is to synthesize compounds which mimic known biologically active compounds. However, since the active moiety or active structural component of the active compound is usually unknown, the process of synthesizing new compounds relies primarily on trial and error and the synthesis and screening of each compound individually. This method is time consuming and expensive since the likelihood of success for any single compound is relatively low.

Rather than trying to determine the particular three-dimensional structure of a protein using crystallography or attempting to synthesize specific peptides which mimic a known biologically active peptide an art has developed with respect to the production of combinatorial libraries. More specifically, those attempting to isolate biologically active peptides produce extremely large numbers of different peptides at the same time within the same reaction vessel. The synthesized combinatorial library is then assayed and active molecules are isolated and analyzed. Combinatorial libraries per se are disclosed within U.S. Pat. No. 5,266,684. U.S. Pat. No. '684 relates almost completely to the synthesis of libraries wherein each of the reaction products in the library is a peptide comprised of the twenty naturally occurring amino acids.

Since pharmaceutically active compounds are often highly substituted heterocycles, the present inventors have found a need for a method to rapidly synthesize a large number of related substituted heterocyclic compounds quickly and relatively inexpensively. This approach would overcome the problem of a separate synthesis for each member of a group of candidate compounds where the structural components conferring biological activity are unknown.

SUMMARY OF THE INVENTION

The invention relates to libraries of cyclic organic compounds and method of producing and assaying such libraries. According to the invention, each cyclic organic compound is constructed from a starting material in the form of a solid surface derivatized with a starting resin. Compounds are reacted with the resin to add or to form a cyclic group. The reactions are preferably carried out using a split resin procedure so that different compounds can be reacted with a plurality of subamounts so as to increase the size of the library. For example, compounds are reacted with a solid support bound starting resin to obtain a compound which includes an aldehyde functional group wherein the aldehyde compound or compounds reacted with it have substituents which are varied such that a mixture of products is obtained. The invention further relates to methods of producing combinatorial libraries of cyclic organic compounds from substrate bound compounds by cleaving the compounds from the support after synthesizing is completed and to assaying libraries of such compounds.

Libraries of the invention are all produced using a solid support derivatized with a starting resin. The starting resin is then subjected to reactants which are sequentially linked together resulting in the formation of a cyclic compound. The sequential linking of reactants may be and preferably is carried out using (1) split-resin methodology and (2) submonomer methodology, both of which are explained below in detail.

A primary object of the present invention is to provide mixtures (libraries) containing large numbers of cyclic organic compounds derived from substrate bound resins which are covalently attached to a solid substrate but may be cleaved from the solid support. The libraries preferably contain at least one biologically active cyclic organic compound.

An important object is to provide an efficient method for quickly synthesizing a complex combinatorial library from starting resins derivatized on a solid support using split-resin methodology in combination with submonomer methodology and obtaining cyclic compounds in the resulting library which compounds are substituted in a manner which dramatically increases the complexity and diversity of the library.

Another object of the invention is to provide a method of obtaining a library of cyclic organic compounds derived from substrate bound resin starting materials which library contains at least one biologically active cyclic organic compound.

The invention comprises libraries of cyclic organic compounds preferably having a cyclic structure which is highly substituted.

Another object of the invention is to provide methodology for screening such cyclic organic compound libraries in order to obtain compounds which mimic to some degree the activity of natural proteins or other biologically active compounds.

Another object of the present invention is to produce novel compounds which are cyclic organic compounds of the invention further bound to a bioactive compound such as a pharmaceutically active drug so as to provide biochemical targeting for the drug via the enhanced binding affinity of the synthesized cyclic organic compound of the invention.

An advantage of the present invention is that the methodology can be used to synthesize and isolate solid support-bound cyclic organic compounds with the strongest receptor binding affinity or other optimized target biological activity.

Another advantage of the present invention is that the cyclic organic compounds and libraries of the invention can be used to explore receptor interactions, i.e., the interaction between such compounds and the natural receptor sites.

Another object of the invention is to provide drug design methodology whereby cyclic organic compounds derived from substrate bound aldehyde starting materials are designed, which compounds have the same or stronger affinity for a natural receptor site as a bioactive protein or other bioactive molecule which binds to the same receptor site.

Another feature of the invention is that the chemical synthesis methodology is used in connection with solid phase reaction techniques, making it possible to produce defined libraries, and the solid phase reaction techniques can be automated to produce cyclic organic compounds and/or libraries in commercial quantities.

Yet another feature of the invention is that the substrate-bound cyclic organic compounds of the invention have not only different structures with respect to the bonds they contain as compared to natural peptides or other bioactive molecules, but have different three-dimensional structures which structures may not be possible with the natural peptides or other bioactive molecules.

These and other objects, advantages and features of the present invention will be come apparent to those persons of ordinary skill in the art upon reading the details of the structure, synthesis and usage as more fully set forth below, reference being made to the accompanying general structural formulas and synthesis schemes forming a part hereof wherein like symbols refer to like molecular moieties throughout.

DETAILED DESCRIPTION

Figure 1:
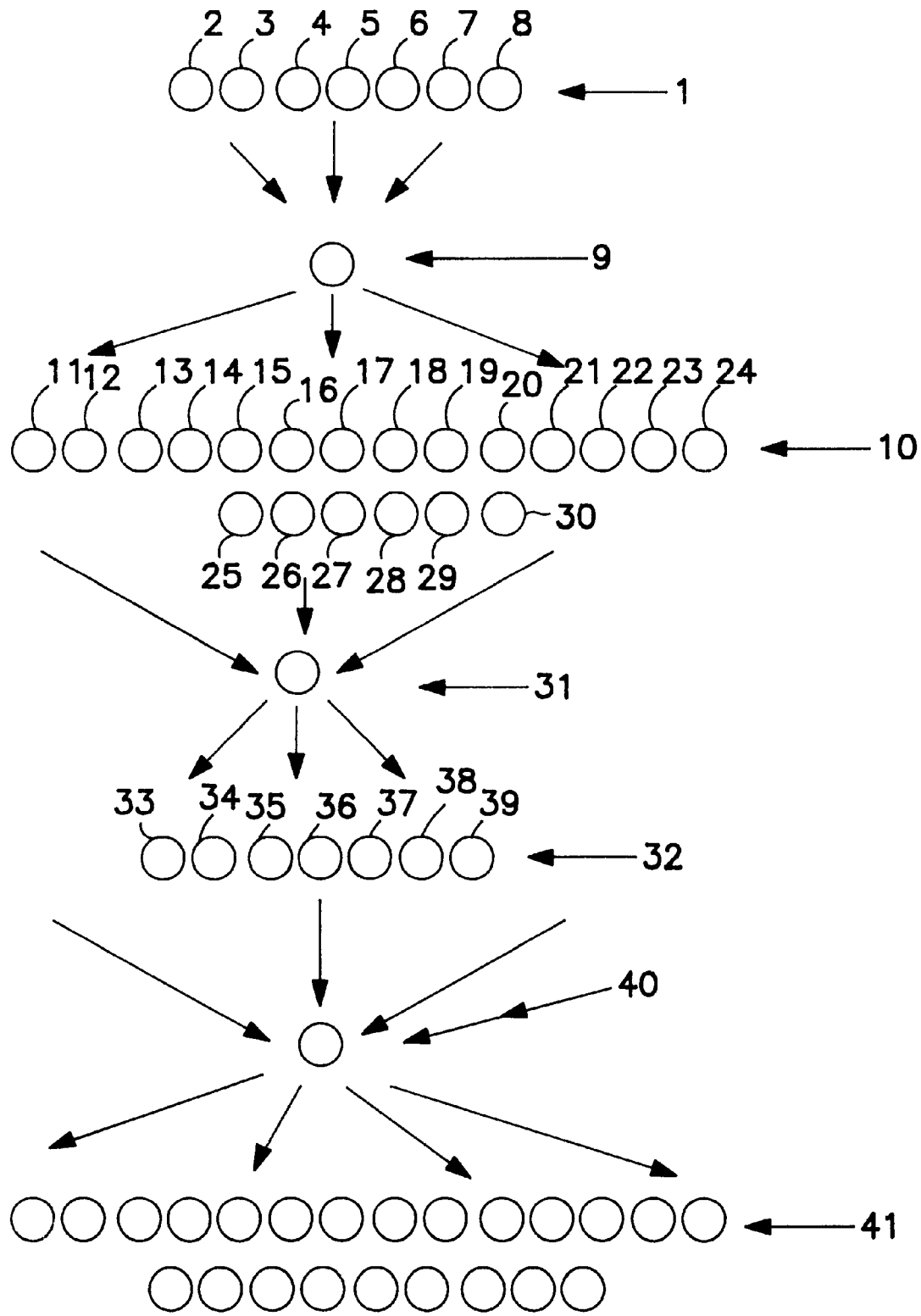
FIG. 1 is a schematic drawing showing the split resin methodology.

Before the present solid phase, resin-derived, cyclic organic compounds, libraries and conjugates, as well as processes for making such are described, it is to be understood that this invention is not limited to the particular cyclic and heterocyclic compounds and their substituents described herein as such compounds and their substituents as well as the methods may, of course, vary. It is also to be understood that the terminology used herein is for the purpose of describing particular embodiments only, and is not intended to be limiting since the scope of the present invention will be limited only by the appended claims.

Throughout this description and the appended claims, it must be noted that the singular forms "a", "an" and "the" include plural referents unless the context clearly dictates otherwise. Thus, for example, reference to "a cyclic organic compound" includes mixtures of such cyclic organic compounds and more than one copy of a molecule, reference to "reactive starting compound" includes reference to mixtures of such reactive starting compounds and/or multiple copies of such starting compounds, and reference to "the method of synthesis" includes a plurality of such methods which will occur to those of ordinary skill in the art upon reading this disclosure.

The present invention includes a variety of different aspects, including novel cyclic or heterocyclic organic compounds and conjugates, libraries of cyclic compounds, processes for synthesizing such cyclic or heterocyclic compounds, libraries and conjugates, and processes for isolating from such libraries cyclic compounds of desired biological activity. Further, within each of these aspects of the invention, the present invention includes a large number of specific embodiments. The essence of the invention involves providing processing technology whereby those of ordinary skill in the art can use the information disclosed and described herein in order to produce and isolate molecules which mimic the biological activity of naturally-occurring molecules or synthetic biologically active molecules but which compounds of the invention have different chemical structures as compared to the natural molecule or synthetic molecule. The word "mimic" is used loosely, in that the molecules produced may have the same activity, greater activity, lesser activity, and/or block the effect of naturally-occurring biologically active molecules or biologically active synthetic molecules.

All publications mentioned herein are incorporated herein by reference for the purpose of disclosing and describing features of the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

A number of terms are defined and used throughout the specification with the following definitions provided for convenience.

Definitions

The terms "library", "combinatorial library", "resin-derived library" and the like are used interchangeably herein to mean a mixture of cyclic organic compounds synthesized on a solid support from one or more solid phase bound resin starting materials. The library will contain 10 or more, preferably 100 or more, more preferably 1,000 or more and even more preferably 10,000 or more cyclic organic molecules which are different from each other (i.e., 10 different molecules and not 10 copies of the same molecule). Each of the different molecules (different basic structure and/or different substituents) will be present in an amount such that its presence can be determined by some means, e.g., can be isolated, analyzed, detected with a receptor or suitable probe. The actual amounts of each different molecule needed so that its presence can be determined will vary due to the actual procedures used and may change as the technologies for isolation, detection and analysis advance. When the molecules are present in substantial equal molar amounts an amount of 100 picomoles or more can be detected. Preferred libraries comprise substantially equal molar amounts of each desired reaction product and do not include relatively large or small amounts of any given molecules so that the presence of such molecule dominates or is completely suppressed in any assay.

The terms "functional group", "functional moiety" and the like are used herein to describe organic groups of molecules comprised of carbon, oxygen, hydrogen and nitrogen. Typical functional groups are attached to the "cyclic compound" component as defined herein and include aldehydes, ketones, carboxylic acids, esters, amides, amines, ethers and nitriles. Preferred functional groups attached to the "cyclic compound" are aldehydes and ketones. The general structure of each of these groups is well known. However, for purposes of this application these groups are defined as per the following definition of "aldehyde" with appropriate modifications for each group.

The term "aldehyde" as used herein shall mean a compound having the following general structural formula

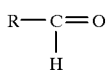

I wherein R is covalently connectable to the carbon atom and a suitable solid substrate or resin and may be a covalent bond or any atom or group of atoms covalently bondable to the carbon atom and a suitable solid substrate or resin. The "R" is preferably alkyl containing 1 to 12 carbon atoms or a substituted alkyl. However, "R" may be any hydrocarbon-based moiety or hydrocarbon-based substituted moiety. The "R" may be a "hydrocarbyl" or a "sidechain" as defined herein.

The term "oligomer" means polymers such as produced by the process of the invention, including homopolymers, copolymers and interpolymers of any length. More specifically, oligomers may be comprised of a single repeating monomer, two alternating monomer units, two or more monomer units randomly and/or deliberately spaced relative to each other. The oligomer is preferably 2–100 monomers, more preferably 2–50, or 2–20, and most preferably 2–6 monomers.

The term "acyl submonomer" refers to an acylating reagent used in the invention. Acyl submonomers comprise a reactive carbonyl or carbonyl equivalent, and a leaving group which may be displaced in a nucleophilic displacement by an amine. "Carbonyl or carbonyl equivalent" includes, without limitation, carboxylic acids, esters, amides, anhydrides, acyl halides, and isocyanates (in the synthesis of polycarbamates of the invention). Esters and amides used will generally be "reactive" forms., e.g., DIC adducts and the like. The acyl submonomer may further comprise a side chain. Suitable acyl submonomers include, without limitation, bromoacetic acid, 3-bromopropionic acid, 2-bromopropionic acid, 2-bromoethylisocyanate, 2-bromoethylchloroformate, 6-phenyl-3-bromohexanoic acid, 4-bromomethyl-benzoic acid, 4-bromomethyl-2-methoxybenzoic acid, 5-bromomethyl-pyridine-2-carboxylic acid, and the like.

The term "amino submonomer" refers to a compound containing an amino group capable of effecting a nucleophilic displacement of the leaving group in an acyl submonomer. The amino group may be primary, secondary, or tertiary. Addition of tertiary amines results in quarternary ammonium salts, and are preferably used as chain terminators (i.e., no further acylation of the oligomer is possible). Presently preferred amino submonomers are primary amines and hydrazides, although amides, carbamates, ureas, carbazides, carbazates, semicarbazides, and the like are also suitable.

The term "sub-monomer" refers to an organic reactant used in the method of the invention which is added to the substrate-bound material in a step of the invention. An "acyl sub-monomer" of the invention (the first sub-monomer of scheme IA) is an acylating agent comprising a leaving group capable of nucleophilic displacement by any amino group, e.g., —NH2, —NRH or —NR$_2$. An "amino sub-monomer" (second sub-monomer of scheme IA, for example) is a displacing agent reactant comprising an —NH$_2$ group.

In another aspect of the invention, submonomers are added sequentially to a solid support or aldehyde derivatized solid support resin to form a backbone which is subsequently cyclized. In the preparation of a peptoid backbone for cyclization, the stepwise addition of submonomers introduces side chains and ring substituents to the final product.

Details of sub-monomer synthesis are described herein, in U.S. application Ser. No. 08/126,539, filed Jul. 18, 1994, now abandoned, which disclosure is herein incorporated by reference.

The term "sidechain" refers to a group attached to the organic compound via a carbon or nitrogen atom. The attachment may be at the ring structure of the cyclic group or on a polyamide backbone of a compound at either a nitrogen or carbon atom. Sidechains may be H, hydroxy, $R_a$, —$OR_a$, —$NR_aR_b$, —$SO_{1,2,3,4}R_a$, —$C(O)R_a$, —$C(O)OR_a$, —$OC(O)R_a$, —$OC(O)OR_a$, —$NR_bC(O)R_a$, —$C(O)NR_aR_b$, —$OC(O)NR_aR_b$, —$NR_cC(O)NR_aR_b$, —$NR_bC(O)OR_a$, —$R_a$—O—$R_b$, —$R_a$—$NR_bR_c$, —$R_a$—S—$R_b$, —$R_a$—S(O)—$R_b$, —$R_a$—S(O)$_2$—$R_b$, —$OR_a$—O—$R_b$, —$NR_aR_b$—O—$R_c$, —$SO_{1,2,3,4}R_a$—O—$R_b$, —$C(O)R_a$—O—$R_b$, —$C(O)OR_a$—O—$R_b$, —$OC(O)R_a$—O—$R_b$, —$OC(O)OR_a$—O—$R_b$, —$NR_bC(O)R_a$—O—$R_c$, —$C(O)NR_aR_b$—O—$R_c$, —$OC(O)NR_aR_b$—O—$R_c$, —$NR_cC(O)NR_aR_b$—O—$R_d$, —$NR_bC(O)$ $OR_a$—O—$R_C$, —$OR_a$—S—$R_b$, —$NR_aR_b$—S—$R_c$, —$SO_{1,2,3,4}R_a$—S—$R_b$, —$C(O)R_a$—S—$R_b$, —$C(O)OR_a$—S—$R_b$, —$OC(O)R_a$—S—$R_b$, —$OC(O)OR_a$—S—$R_b$, —$NR_bC(O)$ $R_a$—S—$R_c$, —$C(O)NR_aR_b$—S—$R_c$, —$OC(O)NR_aR_b$—S—$R_c$, —$NR_cC(O)NR_aR_b$—S—$R_d$, —$NR_bC(O)OR_a$—S—$R_c$, —$OR_a$—$NR_bR_d$, —$NR_aR_b$—$NR_cR_d$, —$SO_{1,2,3,4}R_a$—$NR_bR_d$, —$C(O)R_a$—$NR_bR_d$, —$C(O)OR_a$—$NR_bR_d$, —$OC(O)R_a$—N—$R_bR_d$, —$OC(O)OR_a$—$NR_bR_d$, —$NR_bC(O)R_a$—$NR_cR_d$, —$C(O)NR_aR_b$—$NR_cR_d$, —$OC(O)NR_aR_b$—$NR_cR_d$, —$NR_cC(O)NR_aR_b$—$NHR_d$, —$NR_bC(O)OR_a$—$NR_cR_d$; where $R_a$, $R_b$, $R_c$ and $R_d$ are each independently alkyl, alkenyl, alkynyl, aryl, aralkyl, aralkenyl or aralkynyl;

where $R_a$, $R_b$, $R_c$ and $R_d$ are each substituted with 0–6 halo, $NO_2$, —OH, lower alkyl, —SH, —$SO_3$, —$NH_2$, lower acyl, lower acyloxy, lower alkylamino, lower dialkylamino, trihalomethyl, —CN, lower alkylthio, lower alkylsufinyl, or lower alkylsulfonyl wherein "lower" indicates 1 to 6 carbon atoms.

The terms "hydrocarbon-based", "hydrocarbon-based substituent" and the like denotes a moiety having a carbon directly attached to the remainder of the molecule and having predominantly hydrocarbon-based character within the context of this invention.

Examples of substituents include the following:

(1) hydrocarbon substituents, that is, aliphatic (e.g., alkyl or alkenyl), alicyclic (e.g., cycloalkyl, cycloalkenyl) substituents, aromatic, aliphatic and alicyclic-substituted aromatic nuclei and the like as well as cyclic substituents wherein the ring is completed through another portion of the molecule (that is, for example, any two indicated substituents together form an alicyclic radical;

(2) substituted hydrocarbon substituents, that is, those substituents containing nonhydrocarbon radicals which, in the context of this invention, do not alter the predominantly hydrocarbon substituent; those skilled in the art will be aware of such radicals (e.g., halo (especially chloro and fluoro), alkoxy, mercapto, alkylmercappto, nitro, nitroso, sulfoxy, etc.);

(3) hetero substituents, that is, substituents which will, while having predominantly hydrocarbyl character within the context of this invention, contain other than carbon present in a ring or chain otherwise composed of carbon atoms. Suitable heteroatoms will be apparent to those of ordinary skill in the art and include, for example, sulfur, oxygen, nitrogen, and such substituents as, e.g., pyridyl, furanyl, thiophenyl, imidazolyl, etc., are exemplary of these hereto substituents. Heteroatoms and preferably no more than one, will be present for each carbon atom in the hydrocarbon-based substituents. There may be no such radicals or heteroatoms in the hydrocarbon-based substituent and it will, therefore, by purely hydrocarbon.

"Hydrocarbon" describes a compound, whereas "hydrocarbyl" and "hydrocarbylene" describe radicals with one or two hydrogens removed respectively. Each are generally composed entirely of hydrogen and carbon atoms but may include a hetero atom, and may be saturated or unsaturated, aliphatic, alicyclic or aromatic. When rings are included the structure usually includes one, two, three, or more rings, which rings may be fused or bridged or spiro-fused.

The terms "cyclic compound" and "cyclic moiety" are used to describe an organic compound or moiety which is hydrocarbon-based as defined above which has a structure characterized by one or more closed rings which may be saturated or unsaturated. A cyclic compound or moiety may be mono, bi, tri, or polycyclic depending on the number of rings present. The terms encompass the three major groups of cyclic compounds: (1) alicyclic, (2) aromatic (also called asene) and (3) heterocyclic.

The term "molecular moiety" encompasses any atom or group of atoms attachable to a nitrogen atom or a carbon atom of the main-oligomer chain, thereby forming a side-chain off of the main chain of any compound being formed such as an oligomer, e.g., in $CH_3(R^1)NC(O)CH(R^2)CH^3$, in which $R^1$ is a molecular moiety attachable to the nitrogen atom of the oligomer main-chain, thereby forming a side-chain attached to the nitrogen atom, and $R_2$ is a molecular moiety attachable to the carbon atom of the oligomer main-chain, thereby forming a side-chain attached to the carbon atom. Thus, it is readily apparent to those of skill in the art of polypeptide or polyamide synthesis that a wide variety of molecular moieties can be used, including but not limited to hydrogen, and hydrocarbyl moieties such as alkyl, aryl and arylalkyl moieties.

"Organic compound" means a molecule comprised of carbon, hydrogen, nitrogen, oxygen, sulphur, and phosphorous atoms. As used herein, an organic compound can be a cyclic or acyclic compound formed entirely of carbon and hydrogen, or it can contain one or more heteroatoms including oxygen, nitrogen, sulphur, and phosphorous atoms.

"Cyclic organic compound" means an organic compound which contains at least one cyclic structure derived from cyclization of the peptoid backbone. The cyclic structure can be a hydrocarbon comprised of carbon and hydrogen and can be aliphatic or aromatic. The cyclic structure may be a heterocycle containing at least one heteroatom in the cyclic backbone. The heterocyclic structure may be saturated or unsaturated. Cyclic structures may be fused or separated within a cyclic compound.

Substituent describes an atom or radical which is part of a first molecule in that it replaces another atom or radical of the first molecule. When a molecule is substituted, it is a derivative of a molecule bearing one or more substituents. Useful substituents in any of the sub-monomers of the invention include halo, alkyl, alkoxy, alkylthio, haloalkyl, haloalkoxy, halothio, disubstituted amino, and the like, which replace an atom such as hydrogen attached to a nitrogen or carbon. A substitutable position is the attachment site of the replaced atom or radical of the first molecule.

A "purine or pyrimidine base" includes the natural nucleoside bases, such as A, T, G, C or U, and also derivatives thereof including those purines and pyrimidines substituted by one or more of alkyl, caboxyalkyl, amino, hydroxyl, halogen (i.e. fluoro, chloro, bromo, or iodo), thiol, or alkylthio wherein the alkyl group contains from 1 to about 6 carbon atoms. Non-limiting examples of purines and pyrimidines include 2,6-diaminopurine, 5-fluorouracil, xanthine, hypoxanthine, 8-bromoguanine, 8-chloroguanine, 8-aminoguanine, 8-hydroxyguanine, 8-methylguanine, 8-thioguanine, 2-aminopurine, 5-ethylcytosine, 5-methylcyosine, 5-bromouracil, 5-ethyluracil, 5-iodouracil, 5-propyluracil, 2-methyladenine, methylthioadenine, N,N-diemethyladenine, 8-bromoadenine, 8-bydroxyadenine, 6-hydroxyaminopurine, 6-thiopurine, 4-(6-aminohexyl/cytosine) and the like.

"Leaving group" means a moiety capable of nucleophilic displacement by an amine, e.g., $—NH_2$. Any leaving group can be used here provided it is readily removed by nucleophilic displacement. Non-limiting examples of leaving groups useful in the invention include halo, such as bromo, chloro, iodo, O-tosyl, O-triflyl, O-mesyl and the like.

The terms "substrate", "solid support" and the like are used interchangeably herein to define any solid material (at room temperature) to which starting resin materials (reactive groups) may be bound. Preferred solid support materials comprise polymeric compounds such as polyethylene and polystyrene compounds and related inert polymeric compounds and as such are generally represented herein by the letter "P". The substrate may be in any shape including sheets, the inside of a cylindrical vessel, or pins but are preferably in the form of spherical beads less than 1.0 cm in diameter more preferably less than 1.0 mm in diameter. A "substrate" or solid support is a conventional solid support material used in peptide synthesis. Non-limiting examples of such substrates or supports include a variety of support resins and connectors to the support resins such as those which are photocleavable, DKP-forming linkers (DKP is diketopiperazine; see, e.g., WO90\09395 incorporated herein by reference), TFA cleavable, HF cleavable, fluoride ion cleavable, reductively cleavable and base-labile linkers. A solid support resin comprises a plurality of solid support particles which can be split into portions for separate reactions and recombined as desired. Thus, when the term "resin" is used with solid support (e.g., solid support resin) the term describes a polymeric material derivatized with a reactive group such as a $—NH_2$ group or other electron donating group such as an hydroxyl group.

"Protecting group" means any group capable of preventing the atom to which it is attached, usually oxygen or nitrogen, from participating in an undesired reaction or bonding, usually in a synthesis reaction. Protecting groups are also known to prevent reaction or bonding of carboxylic acids, thiols, and the like. Such groups and their preparation and introduction are conventional in the art and include salts, esters and the like.

"Electron donating group (EDG)" means a moiety covalently attached to a reactant with EDG is capable of increasing electron density in other parts of the reactant. Non-limiting examples of electron donating groups useful in the invention include alkyl, amine, hydroxyl, alkoxy, and the like.

By "electron withdrawing group (EWG)" is meant a moiety covalently attached to a reactant which EWG is capable of activating nucleophilic addition of a portion of a polyamide backbone to the reactant. Non-limiting examples of leaving groups useful in the invention include nitro, carbonyl, cyano, sulfone and the like.

By "driving the reaction to completion" or to "substantial completion" is meant that sufficient reactant is added (under sufficient conditions e.g., time and temperature) to allow all or substantially all of the solid-support bound intermediate compound is derivatized by the reactant. "Driving the reaction to substantial completion" means performing a reaction under conditions in which the concentrations of reactants, catalysts, temperature, and other conditions are appropriate to cause greater than 80%, preferably greater than 90%, more preferably greater than 95%, still more preferable 99% or more of the solid-support bound intermediate compound (e.g., resin) is reacted with the added reactant such that all detectable intermediate resin is reacted.

"Retrievable amount" means an amount of a compound in a mixture which compound is present in a concentration such that a recoverable amount is separable from the other components of the mixture by techniques available in the art at the time of separation. Preferably, at least 50 pmol, more preferably 100 pmol of compound is present in the mixture when the components of the mixture are present in approximately equal molar amounts.

"Analyzable amount" means an amount of a compound that is present in a mixture such that the compound can be detected and identified in the mixture. Preferably at least approximately 10 pmol, more preferably 50 pmol of compound is present in the mixture when the components of the mixture are present in approximately equal molar amounts.

The terms "pool" and "pooled amount" mean a combining of derivatized or underivatized solid support particles to form a mixture. Pooled materials contain intermediates or final products in the preparation of a library.

The term "subamount" is a portion of a pooled amount which has been divided out of the pool. Each subamount is preferable equal in size to all other subamounts. Subamounts are shown in FIG. 1 and are used in connection with the split resin method described herein. A pooled amount include the amounts 9, 31 and 40 of FIG. 1 and subamounts include 2–8, 11–24, etc.

General Methodology

The methodology begins by derivitizing an electron donating compound onto a solid-phase support. In general the solid support has a commercially available resin attached such as a Rink or Merrifield Resin attached. If P represents the support the support with a resin thereon is represented by P—XH where X is O or NH. Where A is any functional group such as an aldehyde group derivatized onto a starting resin and is represented by P—XH—A. The functional group such as an aldehyde or ketone is subjected to cyclization by reacting with the functional moiety so as to form cyclic compounds comprised of substituted and unsubstituted rings providing a diverse library of compounds. For example, an aromatic aldehyde A is bound to a support via a RINK amide for P—NH—A. The aldehyde is reacted simultaneously with an amide such as sarcosine and an ester such as dimethylmuconate. The compounds react with this aldehyde group and cyclize. Substituents on the resulting product can be varied by providing a mixture of reactants wherein substituents on the reactants are different. For example, the methyl group on the sarcosine and the two methyl groups on the dimethylmuconate can be independently varied to other alkyl moieties.

The order in which the compounds are reacted, their structure, as well as the reaction conditions determines the structure of the product. However, it can be readily seen that the synthetic scheme presented above have several features in common for synthesizing relatively complex molecules from small, substituted molecules in a sequential, stepwise procedure. In each case, a linear substituted backbone is formed and then a cyclization reaction generates a highly substituted cyclic product.

The common features of the synthetic methods described herein will first be described.

The methodology begins by providing a plurality of solid support surfaces e.g., 3 or more, 10 or more, 1,000 or more, 10,000 or more, etc., polymeric beads. The use of large numbers of support surfaces is important with respect to the application of the "split resin" methodology described herein which significantly adds to the power of the invention particularly when combined with the submonomer methodology. The support surfaces are derivatized by reacting them with an electron donating group. This group or resin (e.g.,— $NH_2$) acts as a starting group for building the rest of the molecule. The starting resin may be subjected to a variety of different types of reactions ultimately leading toward the formation of a cyclic compound which is substituted with a functional group e.g., an aldehyde of ketone. For example, the starting resin may be reacted with a submonomer reactant as defined herein. Submonomer units may then be sequentially reacted with each previous group to build a chain of any desired length. For example, if "P" is the solid surface, "EDG" is an electron donating group and "SM" is a submonomer as defined herein the reaction could proceed as follows:

1) P-EDG
2) P-EDG-SM
3) P-EDG-SM-SM

In place of reacting the starting resin with a submonomer it may be reacted with an electron withdrawing group of a cyclic compound. If such a cyclic compound is represented by "CC" the reaction can proceed as follows:

1) P-EDG
2) P-EDG-CC

In place of reacting the starting resin (EDG) with a cyclic compound it may be reacted with a ring forming compound, i.e., a compound which is reacted with one or more additional compounds to form a ring. If "RFC" is a ring forming compound the reaction might proceed as follows:

1) P-EDG
2) P-EDG-RFC+RFC
3) P-EDG-CYCLIC COMPOUND

In all of the above-described general reactions the first reactant is reacted with a prepared (i.e., with an XH group thereon) solid support such that substantially all of the reactive sites on the solid support are occupied by a covalently attached reactant. The first reactant is generally reacted with an NH$_2$ group which is bound to the support. A compound capable of reacting with the first reactant (which then acts as the starting resin) is then reacted with a reactive group on the first reactant.

The method of portioning (creating subamounts) and recombining reacted solid supports is a feature of the submonomer method of cyclic peptoid synthesis which allows the production of mixtures of highly substituted cyclic structures. Mixtures of products result from two features of the invention: 1) the combination and relative positions of variable substituents on the submonomer compounds and, 2) from portioning and recombining reacted solid support particles at selected submonomer additions to produce a mixture of precursor linear peptoids prior to cyclization. The number of different product compounds in a mixture increases with 1) the number of different first reactant compounds attached to a solid resin; 2) the number of different second compounds reacted with the first reactant compound; and 3) the number of variable substituents on each first and second compound.

In one embodiment of the invention a submonomer component is attached to a —NH$_2$ resin derivatized onto the support. The submonomer component has the following general structural formula:

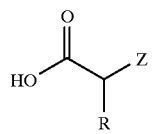

where Z is a halogen (preferably Br) and R is any moiety attached to the carbon atom and may be H or a hydrocarbyl moiety e.g., —CH$_3$. The term "submonomer" is defined above and specific examples are provided.

When the submonomer is reacted with P—NH$_2$ the result is as follows:

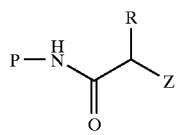

At this point a cyclic organic compound with a functional moiety thereon is reacted with the halogen atom as follows:

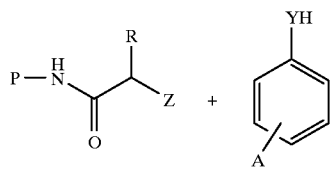

wherein R and Z are defined above, A is any moiety containing a functional group and Y is S,O or NH.

The reaction is carried out under appropriate time and temperature conditions in an appropriate solvent and yields:

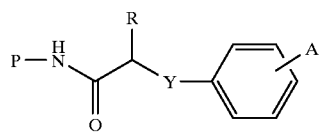

In order to create large libraries a mixture of different submonomer groups with different "R's" thereon are reacted with the starting resin and thereafter a mixture of different cyclic compounds are reacted with the halogen wherein the mixture includes cyclic compounds substituted with a substituent such as a functional group, a "side chain" as defined above or "hydrocarbyl" as defined above. A defined library can be produced by using the "split-resin" methodology as described herein.

In accordance with the present invention, various methodologies are applied for the production of libraries of cyclic organic compounds. More specifically, the method involves preparing mixtures of distinct, unique and different cyclic organic compounds in the same reaction vessel and on a solid phase support. That is, the cyclic organic product compounds within the reaction vessel are different from one another and each of the cyclic organic product compounds in the reaction vessel is present in retrievable and analyzable amounts. By combining submonomer compounds in relative quantities and applying the split resin method such that each reaction is driven to substantial completion, the resulting mixture of cyclic organic compounds will contain each reaction product in a predictable and defined amount and in an amount sufficient such that the cyclic organic compounds can be retrieved and analyzed. The resulting amounts of each of the cyclic organic compounds is predictable in that the amount of derivatized solid support used in each reaction is controlled and each subsequent reaction is driven to completion.

In accordance with a general aspect of the invention, individual cyclic organic compounds are produced using methodology such as solid-phase synthetic techniques after immobilizing a precursor compound such as a precursor aldehyde compound on a solid support such that the reactive moiety (e.g., reactive aldehyde moiety) is available to react with a cyclic compound or a submonomer compound which, in turn, is reacted with one or more subsequent submonomers, and then cyclized. Cyclized compounds (e.g., aldehyde derivatives) can remain attached to the solid support and assayed or cleaved from the support and used in an assay. Cleavage of a cyclized compound (e.g., aldehyde derivative) can also be performed before retrieval or before use, as necessary.

Since the variety of cyclized compounds prepared by the submonomer method is partially controlled by the order of submonomer reaction, it is readily seen that particulate solid support can be apportioned and recombined with each subsequent submonomer reaction such that a mixture of linear aldehyde derivatives is formed when the portions are combined prior to cyclization.

Split Resin Method

Split resin methodology can be applied to the present invention to improve the efficiency of the synthesis and make it possible to dramatically increase the size of the resulting library reaction product. The split resin method comprises splitting a set of the same or mixture of different starting resins derivatized onto supports (e.g., beads) into equal pools. Each of the pools is coupled to a reactant. Different reactants are preferably used with each pool and each reaction is driven to substantial completion. After each reaction is complete the pools are recombined to a single pool to provide the desired library. The process can be repeated any number of times to increase the size of molecules being synthesized on the support and to increase the number of different molecules in the resulting library. The split resin methodology was first applied to the synthesis of large combinatorial libraries of peptides in U.S. Pat. No. 5,182,366, issued Jan. 26, 1993 which is incorporated herein by reference to disclose and describe basis aspects of the split resin method.

FIG. 1 is a schematic drawing of how the split resin methodology is carried out. In step 1 the subamounts of beads 2–8 are reacted so that all the reactive sites thereon occupied by the resin (e.g., NH) are reacted with a reactant (e.g., a submonomer as described herein). The reaction of each of the subamounts 2–8 is driven to completion. The reacted subamounts are then recombined in Step 9. In Step 10 the amount from 9 is divided into subamounts 11–30 and each subamount is reacted with a different reactant and the reactions are each driven to completion. The subamounts 11–30 are then recombined in Step 31 and in Step 32 divided into subamounts 33–39. The subamounts are combined in Step 40 and can be divided into subamounts again in Step 41.

The reacting-combining-splitting-reacting steps can be repeated any desired number of times to increase the size and diversity of the library. Further, as shown in FIG. 1 the combined subamounts can be split into any desired number of subamounts in the next steps. In that each reaction is always driven to completion no reaction product will dominate the other and a mixture containing equal molar amounts of each reaction product can be readily obtained.

The split resin method can be applied to the general methodology described above. Specifically, P—NH$_2$ is divided in a plurality (3 or more, preferably 5 or more, more preferably 10 or more) subamounts. Each subamount of P—NH$_2$ is reacted with a different submonomer having the following structure:

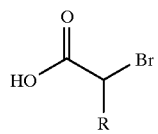

wherein the "R" moiety is varied and each reaction is driven to completion. Although "R" can be any moiety attachable to the carbon atom including any "R" as defined above, "R" is preferably selected from the group consisting of H, —CH$_3$, —CH$_2$CH$_3$, —CH(CH$_3$)$_2$, —CH$_2$—CH$_2$—CH$_3$, =CH$_2$ and phenyl. The structure shown includes a single "R". However, two "R" groups may be attached to the same carbon atom and may be different.

The reaction product obtained in each subamount is then recombined to form a new pool. The recombined mixture or pool is then divided into a plurality of subamounts. Each subamount is then reacted with a different substituted cyclic compound such as a substituted cyclic ketone or aldehyde and each reaction is driven to completion. The reaction product obtained in each subamount is then recombined to provide a final pool which is the desired library of cyclic compounds on a solid support. Receptors can be tested against the library or cleaved from the support and tested against receptors on a solid support.

Submonomer Method

The submonomer methodology is applicable to adding amino acid or amino acid-like monomer units to a chain. This method is particularly useful and efficient when used in combination with the above described split resin methodology. In the basic method each monomer is synthesized directly on a solid substrate (support) from two reactants which are referred to herein as sub-monomers. The following description is specific to the syntheses of amino acid-like compounds (also known as peptoids) but may be applied to cyclization reactions used in forming cyclic compounds.

Each monomer is produced by a synthesis cycle comprising two steps. The first step comprises acylation of a substrate-bound amine carried out using a first submonomer acylating agent comprising a leaving group capable of nucleophilic displacement by an amine e.g., —NH$_2$, such as a haloacetic acid. The second step of the monomer synthesis cycle comprises the introduction of a side-chain by nucleophilic displacement of the leaving group, such as halogen or tosyl, by providing a sufficient amount, usually an excess, of a second sub-monomer displacing agent comprising an amine, e.g., —NH$_2$ group, such as a primary amine. This two-step process is shown within Reaction Scheme I.A.

However, it should be noted that Reaction Scheme I.A can also be carried out in reverse, as is shown within Reaction Scheme I.B. More specifically, it is possible to begin the reaction not with the "substrate-bound amine" as per Reaction Scheme I.A, but to begin the reaction with the acylating agent sub-monomer bound to the substrate. Accordingly, the carboxylic acid group extends from the surface of the substrate and is reacted, in the first step, with an amine. At this point, an amine group now extends outward from the substrate, and is subjected to acylation using a sub-monomer acylating agent as per the first step of Reaction Scheme I.A described above.

The basic two-step process of Reaction Scheme I (A or B) produces a monomer unit and can be repeated to produce polymers (as per formula V below) of any desired length as per monomers of structure I below. The variables shown in the structures can be changed to obtain a desired result. Further, the basic sub-monomer structures can also be changed as below to obtain different monomer/polymer structures as in structures II, III and IV.

SCHEME I.A
Solid-phase assembly of an N-substituted oligomers from two sub-monomers

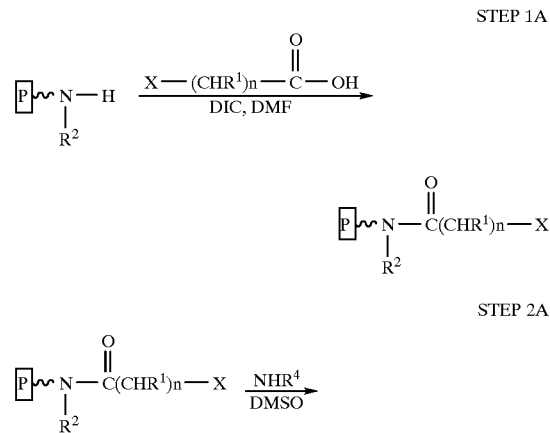

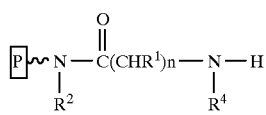

SCHEME I.B
Solid-phase assembly of an N-substituted oligomers from two sub-monomers

STEP 1B

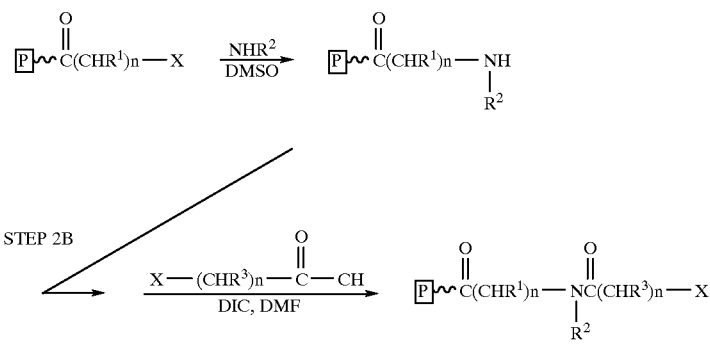

STEP 2B

In each of the above, "P" is the solid phase surface, each $R^1$ and $R^3$ are, independently, any molecular moiety attached to a carbon atom, $R^2$ and $R^4$ are, independently, any molecular moiety attached to a nitrogen atom, and n is an integer of from 1–10 (preferably 1 or 2). Any of $R^1$, $R^2$, $R^3$ and $R^4$ may include the twenty different side-chain moieties attached to the twenty natural amino acids, i.e., —H of glycine; —$CH_3$ of alanine; —$CH(CH_3)_2$ of valine; —$CH_2CH(CH_3)_2$ of leucine; —$CH(CH_3)CH_2CH_3$ of isoleucine; —$CH_2OH$ of serine; —CHOHCH$_3$ of threonine; —$CH_2SH$ of cysteine; —$CH_2CH_2SCH_3$ of methionine; —$CH_2$—(phenyl) of phenylalanine; —$CH_2$—(phenyl)—OH of tyrosine; —$CH_2$—(indole group) of tryptophan; —$CH_2COO^{31}$ of aspartic acid; —$CH_2C(O)(NH_2)$ of asparagine; —$CH_2CH_2COO^{31}$ of glutamic acid; —$CH_2CH_2C(O)NH_2$ of glutamine; —$CH_2CH_2CH_2$—N—(H)—$C(NH_2)^+$—$NH_2$ of arginine; —$CH_2$—(imidazole)$^+$ group of histidine; and —$CH_2(CH_2)_3NH^+$ of lysine.

Reaction Scheme I (A and B) includes some abbreviations which refer to reagents used in connection with the invention. For example, DMSO refers to dimethylsulfoxide, DIC refers to N,N-diisopropyl carbodiimide, and DMF refers to N,N-dimethylformamide.

Each step of the two-step method is usually conducted at about ambient temperature of 20° C. and pressure of 1 atmosphere. However, the reaction can also be carried out over a wide range of temperatures between about 5° C. to about 80° C., and varies depending on the solvent used. Depending on the temperature, the time of the two-step Reaction Scheme I can vary within the range of about 5 minutes to about 24 hours. The above temperature, times and reagents are applicable to carrying out the reaction at atmospheric pressure. Other pressures may be employed.

When the sub-monomers are liquids, each step can be conducted in the absence of a solvent. However, an inert solvent is used when the sub-monomer is a solid or to facilitate the reaction. Suitable inert solvents include ethers, such as dioxane, blocked amides, such as dimethylformamide, sulfoxides, such as dimethylsulfoxide, and the like.

The ratio of the reactants can vary. However, for highest yields it is desirable to provide an excess of sub-monomer of from about 1.01 to 10 times the amount of substrate-bound material, preferably, from about 1.5 to 5 times the amount of substrate-bound material.

In the two-step cycle shown in Scheme I, the secondary amine bound to the substrate is preferably an amine prepared from a primary amine, and is bound (using conventional methodology) to a substrate support base surface or solid phase (represented by the letter "P").

The first step of the cycle is the acylation which is carried out by reacting a first sub-monomer comprising an acylating agent comprising a leaving group capable of nucleophilic displacement by an amine, e.g., —$NH_2$, such as a haloacetic acid, and especially a bromoacetic acid representatively illustrated in Scheme I with the substrate-bound secondary amine to obtain an acylated amine.

The second step of the two-step monomer synthesis method of the invention is where the backbone nitrogen and side-chain or $R^2$ group of the monomer unit is added. In the second step, the acylated amine is reacted with a sufficient amount of a second sub-monomer comprising an —$NH_2$ group, such as a primary amine or secondary amine, alkoxyamine, semicarbazide, carbazate, acyl hydrazide or the like, which includes the $R^2$ group (i.e., the side-chain group), which is to be added at this monomer position in the oligomer. The reaction of the second sub-monomer is preferably accomplished by adding a sufficient amount, usually an excess, of the second sub-monomer which causes a nucleophilic displacement of the leaving group, which is representatively illustrated as the bromine shown in Scheme I.

Application of Split Resin/Submonomer Methodolovy

A primary object of the invention to quickly and efficiently provide very large libraries of cyclic organic compounds (e.g., libraries containing 10 to 10,000 or more compounds) on a solid support. This object is most readily obtained by the use of split resin methodology alone or with submonomer methodology. The method begins by providing a plurality of solid support surfaces which are generally in the form of small polymeric beads. The polymeric beads are represented by the letter "P" and are derivatized by the addition of starting resin which is an electron donating group represented by XH where X is generally NH or O. The electron donating group may be a larger molecule which includes an electron donating group such as the XH group thereon.

The derivatized beads are then divided into 2 or more subamounts. The number of subamounts can be in the thousands but is more typically around 10 to 30.

Each subamount is reacted with a first reactant which may be a submonomer of the following formula:

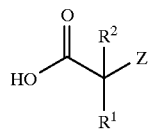

wherein $R^1$ and $R^2$ are each independently any moiety covalently attachable to the carbon atom and Z is a halogen atom—preferable Br.

Alternatively the resin of each subamount is reacted with a cyclic compound reactant having the following general structure

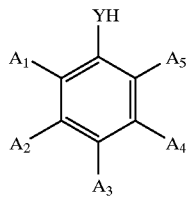

wherein Y is O, S, or NH and each $A_1$, $A_2$, $A_3$, $A_4$ and $A_5$ is independently H or a hydrocarbonyl or a functional group moiety such as an aldehyde, a carboxylic acid, an ester, amide, an amine, a nitrile, or a ketone. Preferred libraries include some compounds with one or more of the functional group moieties on the cyclic structure, most preferably at least one aldehyde or ketone.

If desired, submonomer reactants and/or cyclic compound reactants can be continually added to each other to create a chain of any desired length. In general, however, only one such reactant compound is added and the reaction is driven to completion before the next recombining or pooling step.

Referring to FIG. 1 the first step can involve providing a plurality of solid support beads 2–8. The pool 1 of beads 2–8 are derivatized with a resin —$NH_2$. Each derivatized bead 2–8 is individually reacted with a different submonomer as shown and defined above. Each reaction is driven to completion to provide

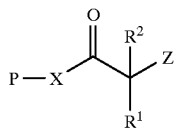

wherein X is preferably NH, Z is preferably Br and $R^2$ and $R^1$ are preferably each independently an alkyl containing 1 to 6 carbon atoms.

Although additional submonomer reactants may be added sequentially to provide a chain of any desired length, in a simple version of the invention each reaction product obtained after a single complete reaction with each subamount is pooled to provide the pool 9 of FIG. 1. The pool 9 is mixed and then divided into subamounts 11–24.

In the less simple version each subamount is then reacted with another (and different) submonomer reactant and each reaction is driven to completion. "Acyl submonomers" are reacted with "amino submonomers" to provide amino acid-like monomer units. The beads may be divided, reacted, and pooled any desired number of times to create a peptide-like chain of amino acid-like monomer units.

In this generalized example the reactions with the second and subsequent submonomers are not shown and the reaction product obtained with the first reaction of a submonomer unit is pooled, divided into subamounts and reacted with a cyclic compound having the following general structural formula:

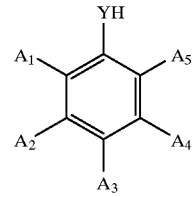

where Y is —O, —SO or —NH, and each of $A_1$, $A_2$, $A_3$, $A_4$ and $A_5$ is independently any moiety attachable to the carbon atom provided that at least one cyclic reactant will comprise any of $A_1$–$A_5$ as a function group—preferably an aldehyde or a ketone. The reaction of each cyclic compound with each subamount is driven to completion to provide the following reaction product:

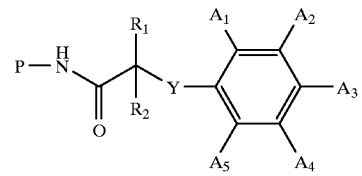

The reaction product of each subamount is then pooled to provide a library of cyclic compounds attached to a plurality of solid support surfaces, i.e., beads. The compounds may be cleaved from the solid supports.

The terminal group may be the substituted cyclic compound as shown above. However, a function group of a substituted cyclic moiety can be further reacted to increase the diversity of the library. An example of how this might be done in the specific instance when the terminal group is a cyclic compound substituted with an aldehyde moiety is provided below.

Reaction With Aldehydes

Libraries of the invention which are synthesized as per the above include an aldehyde functional group on the last added reactant. The diversity of the library can be increased by reacting the aldehyde group via one or all of three known types of reactions.

First, an aldehyde such as an aromatic aldehyde can be reacted with R—$NH_2$ to obtain imine formation as follows:

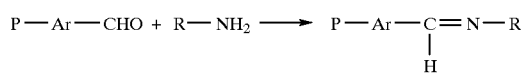

wherein Ar is any aromatic moiety and P and R are as defined above.

Second, an aldehyde such as an aromatic aldehyde can be subjected to Knoevenknagel type reactions to obtain a reaction product as follows:

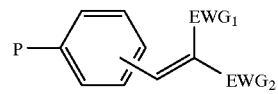

wherein EWG$_1$ and EWG$_2$ are each, independently, electron withdrawing groups and P and Ar are defined above. Preferred electron withdrawing groups include COR, CN, CO$_2$R, SO$_2$R, SOR and SR.

Third, an aldehyde such as an aromatic aldehyde can be subjected to Wittig type reactions to obtain a reaction product as follows:

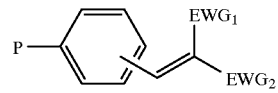

wherein P, Ar, R and EWG are as defined above.

In the above structure the aromatic ring is shown attached directly to the solid support surface. This is done here and elsewhere in the application for purposes of simplicity in that the aromatic ring must be connected to the support surface via an appropriate functional group—generally an NH$_2$ group on the aromatic ring or derivatized on the support. The NH$_2$ group is often referred to as the resin. Thus the above structure could also be shown as:

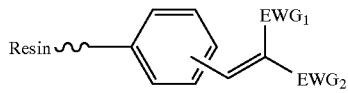

Aldehydes for Forming Ring Structures

After a compound having an aldehyde group thereon is synthesized on a solid support (as per the "General Methodology" section above) the aldehyde group can be reacted with a variety of different compounds to form a four, five or six-membered ring structure. An example of forming a four-membered ring is as follows:

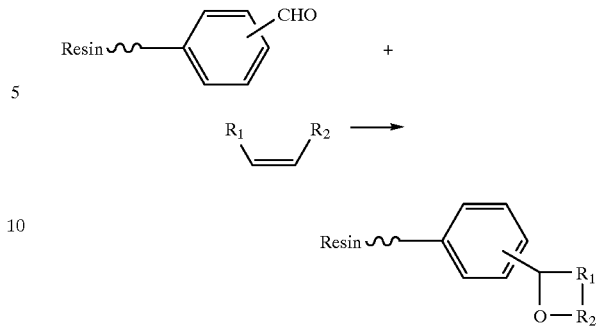

Ar and P are defined above and R$^1$ and R$^2$ are independently any R as defined above.

An example of forming a five—membered ring is as follows:

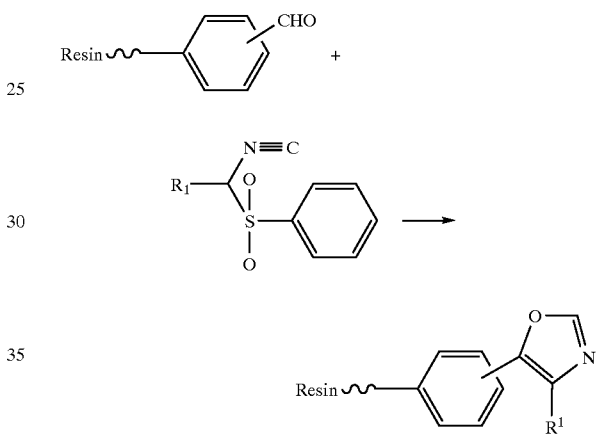

An example of forming a six-membered ring is as follows:

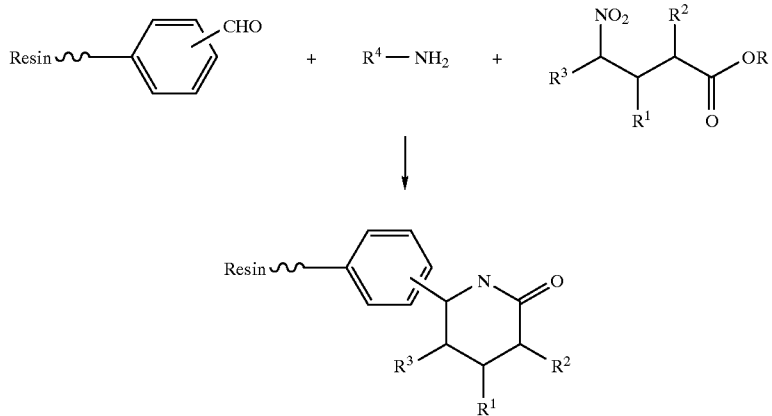

wherein each of R, $R^1$, $R^2$, $R^3$ and $R^4$ are independently defined as R above.

Submonomer units may be sequentially reacted with each other to form peptide or peptide-like backbone structures. The reactions can proceed using split resin methodology. To carry out the submonomer method an acyl submonomer is reacted with an amino submonomer. An acyl submonomer comprises a reactive carbonyl or carbonyl equivalent and a cleaving group which may be displaced in a nucleophilic displacement by an amine. Suitable acyl submonomers include, without limitation, bromoacetic acid, 3-bromopropionic acid, 2-bromopropionic acid, 2-bromoethylisocyanate, 2-bromoethylchloroformate, 6-phenyl-3-bromohexanoic acid, 4-bromomethyl-benzoic acid, 4-bromomethyl-2-methoxybenzoic acid, 5-bromomethyl-pyridine-2-carboxylic acid, and the like.

The acyl submonomer is reacted with an amino submonomer. Presently preferred amino submonomers are primary amines and hydrazides, although amides, carbamates, ureas, carbazides, carbazates, semicarbazides, and the like are also suitable. In that any of the submonomer units can be substituted as with a "hydrocarbyl" or "sidechain" it is possible to react a different submonomer with a large number of different subamounts and drive each such reaction to completion when applying the split resin methodology.

Preparation of Cyclic Peptoids Via the Sub-monomer Method

Cyclic peptoids have been prepared by the sub-monomer method. A general Reaction Scheme for such is shown below.

SUB-MONOMER CYCLIZATION

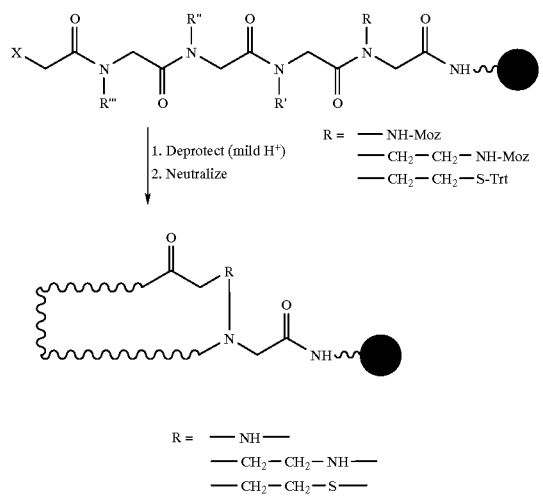

The key reaction to effect cyclization is the displacement of an N-terminal bromoacetamide with a side-chain nucleophile, generating a "head-to-side-chain" cyclic structure on the resin. The side-chain nucleophile is incorporated at the desired portion of the oligomer via standard sub-monomer conditions. Typical nucleophiles are thiols and amines which can be protected. Preferred sub-monomers for this purpose are Moz-NH-$CH_2$-$CH_2$-$NH_2$, Alloc-NH-$CH_2$-$CH_2$-$NH_2$ and Trt-S-$CH_2$-$CH_2$-$NH_2$. The oligomer is then elaborated until the desired length and is terminated with a bromoacetamide group. The side-chain nucleophile is then selectively deprotected and allowed by cyclize.

Specific examples of cyclic peptoids produced and the percentage yield obtained are put forth below. Examples of cyclic compounds having specific ring structures and which are derived from peptoids are provided herein in Examples 19–31.

TRIMERS

| R''' | R'' | R' | MH+ | Yield (%) |
|---|---|---|---|---|
| methoxyethyl | benzyl (phenethyl) | methoxyethyl | 536 | 15 |
| cyclopentylmethyl | cyclopentylmethyl | cyclopentylmethyl | 575 | 29 |
| benzyl | benzyl | benzyl | 600 | 25 |
| 4-hydroxyphenethyl | 4-biphenylmethyl | phenethyl | 705 | 20 |

-continued

| R''' | R'' | R' | MH+ | Yield (%) |
|---|---|---|---|---|
| (diphenylmethyl-ethyl) | (diphenylmethyl-ethyl) | (diphenylmethyl-ethyl) | 870 | 45 |

Utility of Libraries of Cyclic Organic Compounds Synthesized on a Solid-Support

Highly substituted cyclic structures can be synthesized on a solid support by combining the submonomer method of the invention with powerful solution phase chemistry. Cyclic compounds containing one, two, three or more fused rings formed by the submonomer method by first synthesizing a linear backbone followed by subsequent intramolecular or intermolecular cyclization.

To most efficiently probe the binding region of a receptor protein or other molecule, it is generally preferred to create a library of cyclic organic compounds having a variety of substitutions and/or ring structures. The variety of structures in a library increases the chance of isolating a compound having desired binding properties. By applying the methods described herein to synthesis of a collection of cyclic organic compounds on a solid support, one may prepare a large group of compounds for screening. For example, one can prepare a library of cyclic aldehydes having a variety of substituents for analysis of the relative receptor binding affinities. The library may be small (approximately 10 different structures) or large (more than 10,000 different structures).

Such libraries are useful for identifying cyclic organic analogs to a naturally occurring bioactive peptide or other molecule which binds with a requisite affinity to the appropriate receptor. For example, if the hypothetical peptide binds to a known cell-surface receptor, one can prepare a culture of cells expressing the cell-surface receptor, apply the library under conditions conducive to binding, and determine the degree to which members of the library bind the cell-surface receptor or elicit a receptor response.

After interacting the cyclic organic compounds of the library with the receptor, the nonbinding compounds are removed by washing. If a large number of cyclic organic compounds exhibit high binding affinity, the binding conditions may be altered so that only the highest affinity cyclic organic compounds remain bound. The resulting selected cyclic organic compounds may then be removed and identified by standard analytical techniques.

If the relevant structure of the active portion of a bioactive molecule to be mimicked is unknown, for example, the method of the invention is employed to simply construct a larger library. Absent clues as to the structural configuration of the peptide or epitope, a "universal" library having a large range of substituent and/or ring structure variations is most useful.

EXAMPLES

The following examples are put forth so as to provide those of ordinary skill in the art with a complete disclosure and description of how to make the compounds and libraries of the invention and are not intended to limit the scope of what the inventors regard as their invention. Efforts have been made to insure accuracy with respect to numbers used (e.g., amounts, temperature, etc.) but some experimental errors and deviation should be accounted for. Unless indicated otherwise, parts are parts by weight, molecular weight is weight average molecular, temperature is in degrees C, and pressure is at or near atmospheric.

The Examples 1–11 relate generally to reactions involving aldehyde groups and Examples 12–27 relate to reactions involving ketone groups all of which groups are generally connected to a cyclic organic compound. Other functional groups could be attached to the cyclic compound and subjected to known types of reactions to increase the diversity of the library.

Experimental Conditions for Pyrrolidine Synthesis
on Resin

General. NMR analyses were performed on a Varian Unity 300 spectrometer. GCMS analyses were performed on a Hewlett Packard 5890 gas chromatograph coupled with an HP 5972 mass selective detector using the following gradient: 250° C. for 10 min., ramp of 10° C./min. to 325° C., and 325° C. for 15 minutes. HPLC analyses were performed using a Waters 600E system, an Alltech Alltima C18 reversed-phase column (5 mm particle size, 4.6×250 mm), solvent system A:B (water:acetonitrile, with 0.1 col % TFA in each) at 25° C., 1.0 mL/min, with UV detection at 220 nM using the following gradient: 5% B to 95% B over 45 minutes.

Example 1

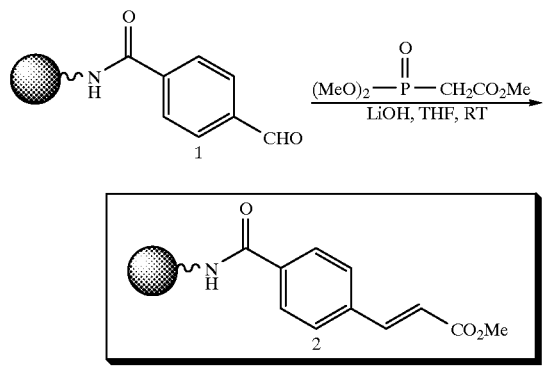

To a 20 mL glass vial containing 2.0 g of 1 on Rink amide resin (1.12 mmol) in 15 mL anhydrous THF was added 517 mg LiOH.H$_2$O(12.32 mmol) and 1.81 mL trimethylphosphonoacetate (11.2 mmol). The vial was capped and shaken for 14 hours at room temperature. The resin was washed with $CH_2Cl_2$, $H_2O$, MeOH and ether consecutively and was dried for 30 minutes under high vacuum. Cleavage of 30 mg of resin with 20% TFA in $CH_2Cl_2$ for 20 minutes yielded pure compound 2. $^1H$ NMR ($CDCl_3$, 300 MHz) :δ 3.84 (s, 3H), 6.51 (d, J=15.6 Hz, 1H), 7.62 (d, J=8.6 Hz, 2H), 7.71 (d, J=15.6 Hz, 1H), 7.85 (d, J=8.6 Hz, 2H). HPLC: 1 peak, $t_R$=21.0 min. GCMS: 1 peak, $t_R$=3.74 min, M=205, M calculated=205).

Example 2
Sarcosine/Sarcosine Derivative Based Pyrrolidines:

The cycloaddition is carried out by combining sarcosine with the aromatic aldehyde bound to Rink amide resin (1), and adding an appropriately substituted alkene to yield 5.

More specifically, into a 2 dram vial with 2.5 mL toulene 110 mg of 1 on resin (0.062 mmol), 220 mg of sarcosine (2.46 mmol) and 419 mg dimethylmuconate (2.46 mmol) were added followed by 30 seconds of argon degassing and tightly capping. The vial is then shaken for 12 hours at 110° C. after which the resin is transferred to a filter and washed with $CH_2Cl_2$, DMF, MeOH, and ether and then dried under high vacuum for 30 minutes. Cleavage of 30 mg of this resin with 20% TFA in $CH_2Cl_2$ for 20 minutes yielded 4 isomers of 5. GCMS: 4 peaks, $t_R$=10.71 min (42.9%), 11.01 min. (4.5%), 11.68 min. (40%), 11.88 min. (12.6%), M=346, M calculated=346.

(2.24 mmol) and 227 μL benzaldehyde (2.24 mmol) were added followed by 30 seconds of argon degassing and tightly capping. The vial is shaken for 12 hours at 110° C. after which the resin is transferred to a filter and washed with $CH_2Cl_2$, DMF, MeOH, and ether and then dried under high vacuum for 30 minutes. Cleavage of 30 mg of this resin with 20% TFA in $CH_2Cl_2$ for 20 minutes yielded 4 isomers of 6. GCMS: 4 peaks, $t_R$=10.96 min. (9.7%), 11.78 min. (21.1%), 12.30 min. (44.6%), 13.17 min (24.6%), M=338, M calculated=338.

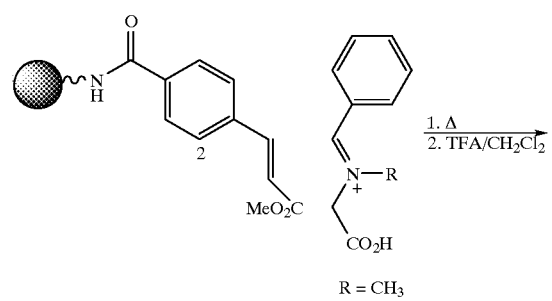

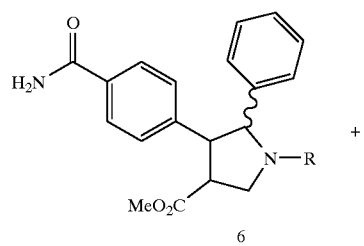

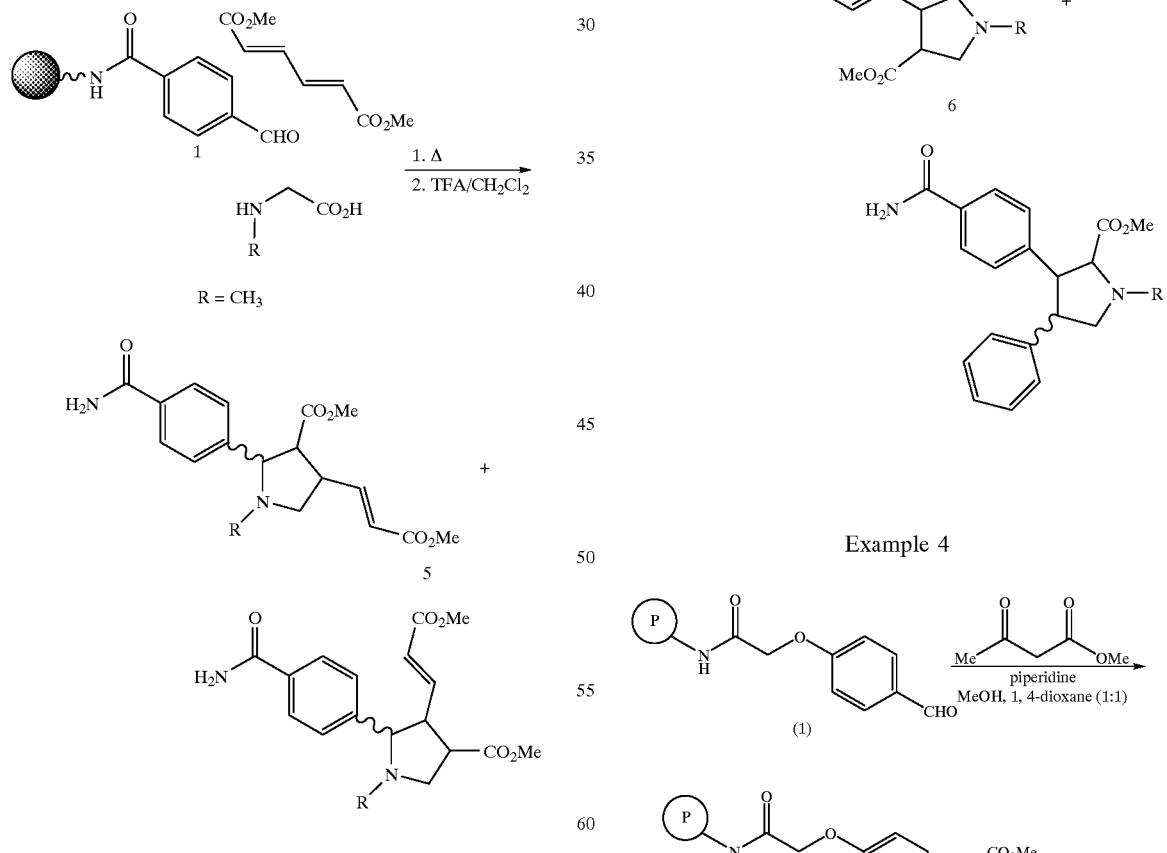

Example 3

In a manner similar to Example 2 sarcosine and an aromatic aldehyde can be combined with 2 to yield 6.

More specifically, into a 2 dram vial with 1.5 mL toulene 100 mg of 2 on resin (0.0565 mmol), 200 mg of sarcosine Example 4

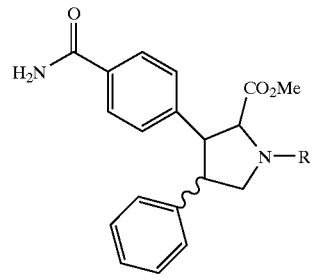

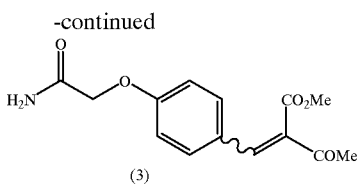

(3)

To a suspension of 1 g (0.43 mmol) resin bound aldehyde 1 in 7 ml of 1:1 MeOH/1,4-dioxane was added 93 μl (2.15 mmol) methyl acetoacetate, followed by 43 μl (43 mmol) piperidine. The reaction mixture was shaken for 24 hours at room temperature and the resin 2 was filtered and washed several times with $CH_2Cl_2$. The resin 2 was treated with 10% TFA in $CH_2Cl_2$ and the product 3 was analyzed by GCMS, which showed a single product having a parent ion of m/z=227, which is the desired product.

Example 5

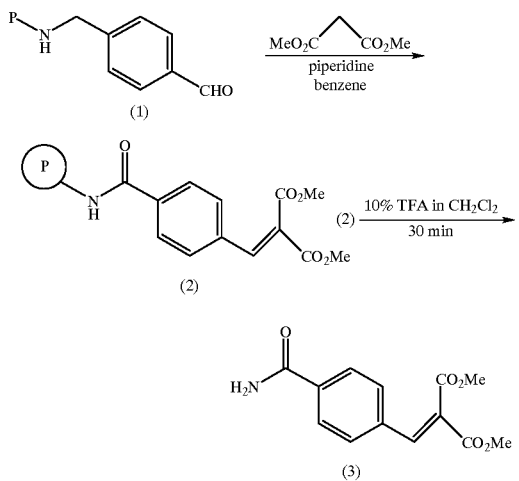

To a suspension of 1 g (0.51 mmol) resin bound aldehyde 1 in 10 ml benzene and molecular sieves was added 292 μl (2.55 mmol) dimethylmalonate, followed by 126 μl (1.28 mmol) piperidine. The reaction mixture was then shaken overnight at room temperature. The resin 2 was filtered and washed several times with $CH_2Cl_2$ and treated with 10% TFA in $CH_2Cl_2$ to give the product 3 in quantitative yield. Analysis by GCMS showed the presence of a single compound having a parent ion with m/z=263, which corresponds to product.

Example 6

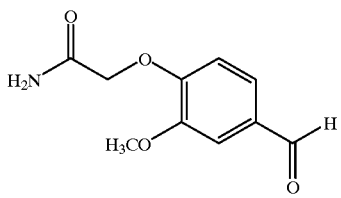

1

To a 23° C. mixture of Rink resin-bound bromoacetamide (50 mg, 0.024 mmol, 0.47 mmol/g) and dry DMF (2 mL)

was added anhydrous $K_2CO_3$ (130 mg, 0.94 mmol) NaI (2 mg, 0.013 mmol) and vanillin (143 mg, 0.94 mmol). After 16 h of vigorous shaking at 75° C., the resulting mixture was diluted with $H_2O$ (10 mL), MeOH (10 mL), THF (2×10 mL), $CH_2Cl_2$ (3×10 mL) and dried under vacuum (150 mm) for 3 h to yield 54 mg of light yellow resin.

To this resin (54 mg, 0.24 mmol) was added a solution of 5% TFA in $CH_2Cl_2$ (2 mL) dropwise. After 15 min at 23° C., the mixture was filtered, the filtrate was washed with $CH_2Cl_2$ (2×5 mL) and the solvent was concentrated to provide 3.7 mg (74%) of 1 as a light yellow oil: $^1H$ NMR (300 MHz, $CDCl_3$) δ 9.86 (s, 1H), 7.48–7.42 (m, 2H), 6.97–6.94 (d, 1H), 4.62 (s, 2H), 3.96 (s, 3H), 3.39–3.15 (br s, 2H)>.

Example 7

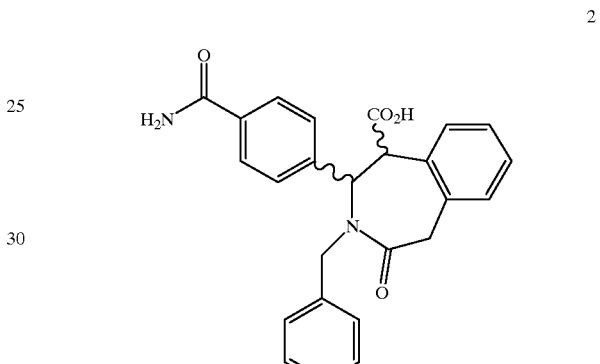

2

To a 23° C. mixture of Rink resin-bound 4-carboxybenzamide benzyl imine (108 mg, 0.085 mmol) and dry benzene (4 mL) was added i-$Pr_2NEt$ (60 μL, 0.34 mmol) and 1,2-phenylenediacetic acid anhydride (59.6 mg, 0.34 mmol). After 16 h of vigorous shaking at 70° C., the resulting mixture was filtered, washed with $H_2O$ (10 mL), MeOH (10 mL), THF (3×10 mL), $CH_2Cl_2$ (3×10 mL) and dried under vacuum (10d mm) for 3 h to yield 122 mg of dark brown resin.

To this resin (122 mg, 0.085 mmol) was added a solution of 5% TFA in $CH_2Cl_2$ (3 mL) dropwise. After 15 min at 23° C., the mixture was filtered, the filtrate was washed with $CH_2Cl_2$ (2×5 mL) and the solvent was concentrated to provide 26.8 mg (76%) of 2 as a dark yellow oil: MS (ESP) m/e calcd for $C_{25}H_{23}N_2O_4$ 415, found 415 (MH).

Example 8

Synthesis of Resin Bound Aldehydes

4-[2', 4'-Dimethoxyphenyl-(4'-formyl-phenylacetamide)]-phenoxy resin {4-Benzaldehyde rink amide resin}

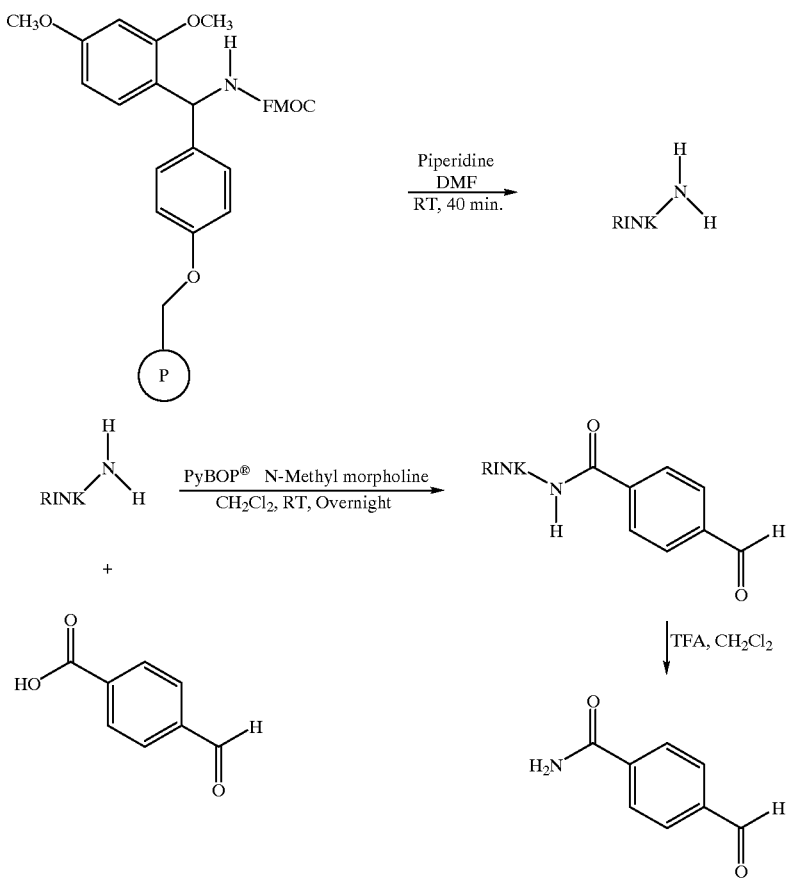

Fmoc Rink amide resin (20.0 g, 9.6 mmol) was shaken in a mixture of piperidine (70 ml) and DMF (80 ml) for 40 min. The resultant suspension was filtered, washed successively with DMF (4×100 ml), water (4×100 ml), THF (4×100 ml), dichloromethane (4×100 ml) and subsequently dried under vacuum.

To a suspension of 4-carboxybenzaldehyde (5.0 equiv, 7.21 g) in dichloromethane (80 ml) was added N-methyl morpholine (5.0 equiv. 5.3 ml) and PyBOP (5.0 equiv. 25.0 g). The resultant solution was allowed to stir for 10 min and added to the dry resin. The suspension was shaken overnight and the reaction was monitored for completion by employing a standard ninhydrin test. The reaction was filtered and the resin was according to the wash cycle reported above. After drying the resin thoroughly a small quantity (40–50 mg) was treated with TFA (40–50 μl) in dichloromethane (2 ml) for 15 min., filtered and the filtrate concentrated in vacuo. The material recovered was analyzed by NMR and GCMS, for the purpose of yield and purity determination.

Example 9

3-Benzaldehyde Rink Amide Resin

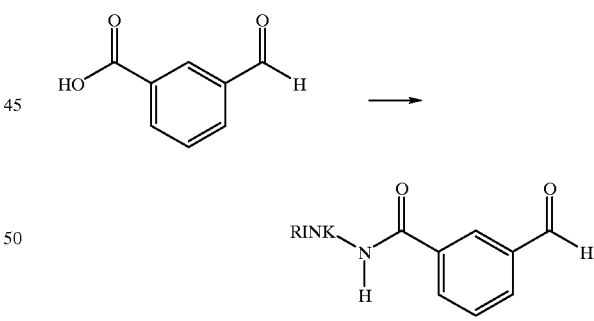

The above method was employed to couple Rink resin (20.0 g) with 3-carboxybenzaldehyde (5.0 equiv. 7.21 g) in the presence of N-methyl morpholine (5.0 equiv. 5.3 ml) and PyBOP (5.0 equiv. 25.0 g).

Example 10

4-Formylphenoxyacetamide Rink resin

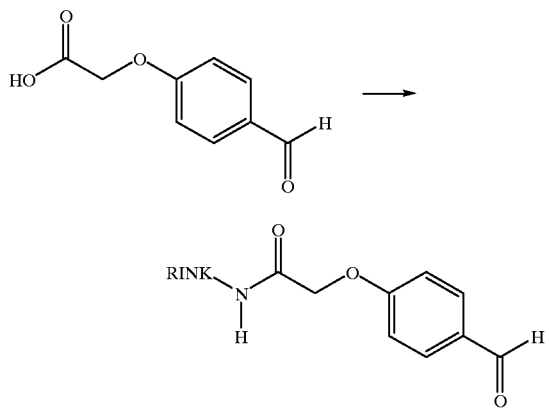

The above method was employed to couple Rink resin (5.0 g) with 4-formylphenxoxyacetic acid (5.0 equiv. 2.16 g) in the presence of N-methyl morpholine (5.0 equiv. 1.32 ml) and PyBOP (5.0 equiv. 6.24 g).

Example 11

4-Bromomethylbenzyl Rink Amide Resin

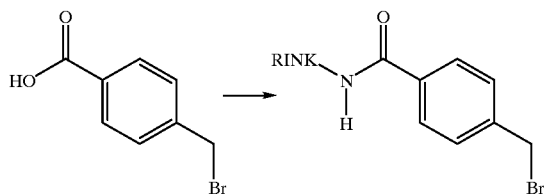

The above method was employed to couple Rink resin (5.0 g) with 4-bromomethyl toluic acid (5.0 equiv. 2.58 g) in the presence of N-methyl morpholine (5.0 equiv. 1.32 ml) and PyBOP (5.0 equiv. 6.24 g).

Example 12

4-Azidobenyl Rink Amide Resin

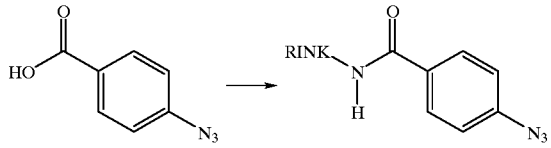

The above method was employed to couple Rink resin (5.40 g) with 4-azidobenzoic acid (3.0 equiv. 1.27 g) in the presence of N-methyl morpholine (5.0 equiv. 0.85 ml) and PyBOP (5.0 equiv. 4.04 g).

Example 13

Synthesis of Cyclic Organic Compounds from a Solid Support-bound Diketone.

Solid support-bound (via Rink linker) diketone IV (70 μmol) is suspended in DMSO (1 mL). Cyanoacetamide (59 mg equivalent to 700 μmol) and piperidine (144 μL, equivalent to 1400 μmol) was added and the reaction mixture was stirred at room temperature. The reaction mixture was drained and washed with DMSO (six times), methanol (three times) and dichloromethane (six times). The solid support was treated with 20% trifluoroacetic acid in dichloromethane for 20 minutes and then filtered. The volatile materials were evaporated under a stream of argon providing the product VII.

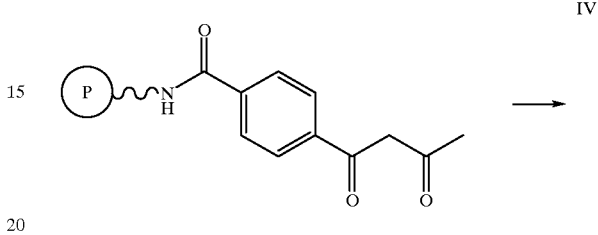

IV

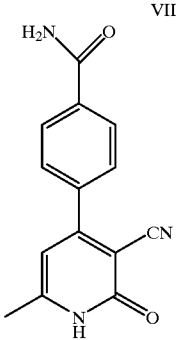

VII

Example 14

Synthesis of Monoketofurans from Solid Support-bound Diketones.

Approximately 70 μmol of solid support-bound IV was suspended in DMF (1 mL). Iodobenzene (184 mg, equivalent to 700 μmol), potassium carbonate (193 mg, equivalent to 1400 μmol) and tetrakis(triphenylphosphine)palladium (O) (39 mg, equivalent to 35 μmol) were added. The reaction mixture was briefly sparged with argon and heated (60–100° C.). The reaction mixture was cooled, drained, and washed with DMF (six times), methanol (three times), and dichloromethane (six times). The solid support was treated with 20% trifluoroacetic acid in dichloromethane for 20 minutes, filtered, and volatiles evaporated under a stream of argon to provided the products V and VI.

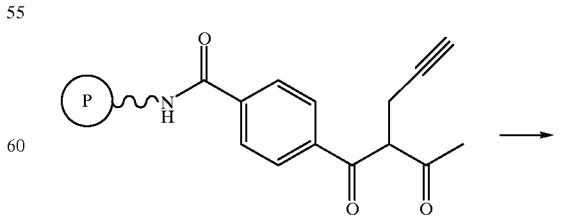

IV

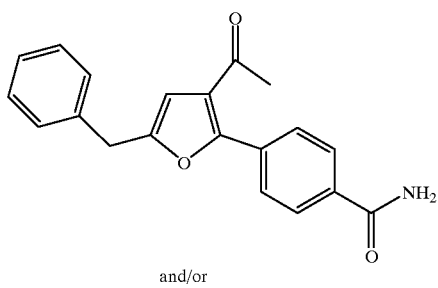

and/or

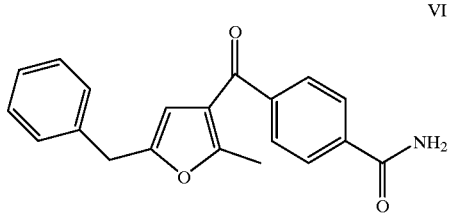

Example 15
Synthesis of N-substituted Pyrazoles from Solid Support-Bound Diketones.

Preparation of Resin

Fmoc Rink amide resin (20.0 g, 9.6 mmol) was shaken in a mixture of piperidine (70 mL) and DMF (80 mL) for 40 min. The resultant suspension was filtered, washed successively with DMF (4×100 mL), water (4×100 mL), THF (4×100 mL), dichloromethane (4×100 mL) and subsequently dried under vacuum.

Synthesis of Support-Bound Monoketone

To a suspension of 4-carboxyacetophenone (5.0 equivalents) in dichloromethane (80 mL) was added N-methyl morpholine (5.0 equivalents) and PyBOP® (5.0 equivalents). The resultant solution was allowed to stir for 10 min and added to the dry resin. The suspension was shaken overnight and the reaction was monitored for completion by employing a standard ninhydrin test. The reaction was filtered and the resin washed successively with DMF (4×100 mL), water (4×100 mL), THF (4×100 mL), dichloromethane (4×100 mL) and subsequently dried under vacuum. After drying the resin thoroughly, a small quantity (40–50 mg) was treated with trifluoroacetic acid (TFA, 40–50 μL) in dichloromethane (2 mL) for 15 min., filtered and the filtrate concentrated in vacuo. The material recovered was analyses by NMR and GC-MS. The structure was consistent that expected for compound 1 detached from the solid support.

Synthesis of Support-Bound Diketone

To prepare the resin-bound diketone, compound 2, resin-bound compound 1 (0.47 mmol, 1.0 g prepared above) was suspended in 12 mL of THF. 15 mg of dibenzo 18-crown-6 and 400 μL of ethyl acetate (4.7 mmol) were introduced under a stream of argon. The suspension was agitated prior to the addition of 2.8 mL of 1M potassium tert-butoxide in THF (2.8 mmol). The reaction was heated to 70° C. for one hour. Cooled resin was then filtered and washed with dichloromethane. A small portion of the resin was treated with 20% TFA in dichloromethane, filtered and volatiles evaporated under a stream of argon. GC-MS and NMR analysis results were consistant with the quantitative conversion to compound 2.

For the preparation of compound 4 on solid support, approximately 100 mg of solid support-bound diketone 2 (47 μmol) was suspended in 1 mL of dry DMSO and 50 μL phenylhydrazine (470 μmol). The reaction vessel was heated to 70° C. with constant agitation for 18 hrs. The cooled, derivatized solid support was then filtered and washed with dimethylformamide and dichloromethane. The solid support was treated with 20% trifluoroacetic acid in dichloromethane for 20 minutes, filtered, and volatiles evaporated under a stream of argon to provide compound 4. Analysis by GC-MS showed quantitative conversion to the desired product (MW=277 by electron impact). NMR of the product in DMSO was consistant with the structure of compound 4 detached from the solid support.

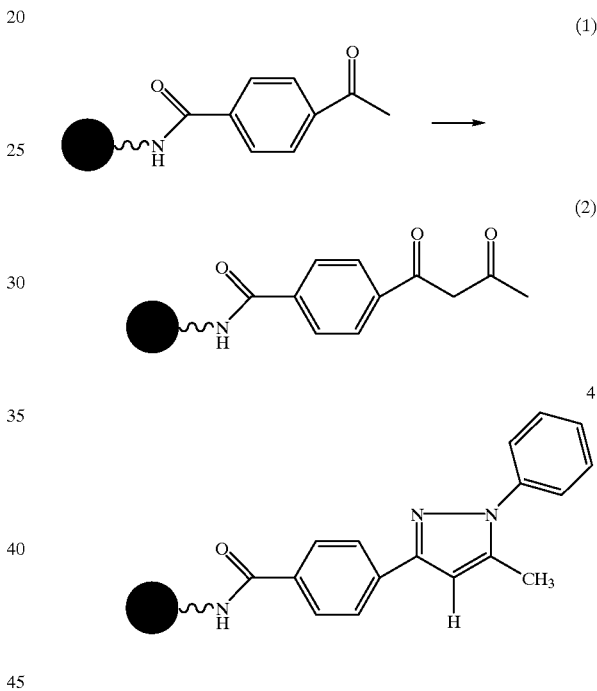

Example 16

Another synthesis of an N-substituted pyrazole

Preparation of a 1:1 mixture of compound 4 and compound 9 was performed as follows. 100 mg of solid support-bound compound 2 (47 μmol) was suspended in 1 mL of toluene, 147 μL DBU (940 μmol), and 50 μL 1-bromobutane (470 μmol) as for the synthesis of compound 8. 50 μL phenylhydrazine (470 μmol) was added and the reaction vessel was heated to 70° C. with constant agitation for 18 hrs as for the synthesis of compound 4. The cooled, derivatized solid support was then filtered and washed with dimethylformamide and dichloromethane. The solid support was treated with 20% trifluoroacetic acid in dichloromethane for 20 minutes, filtered, and volatiles evaporated under a stream of argon to provide a 1:1 mixture of compound 4 and compound 9 by GC-MS analysis.

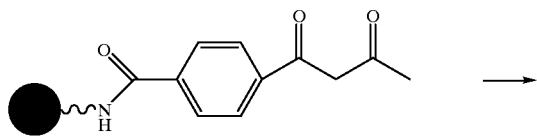

2

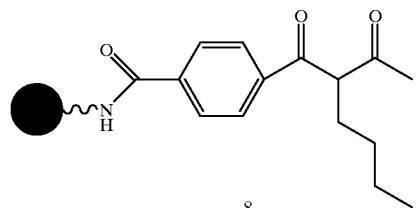

8

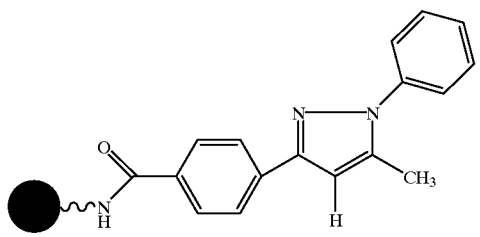

4

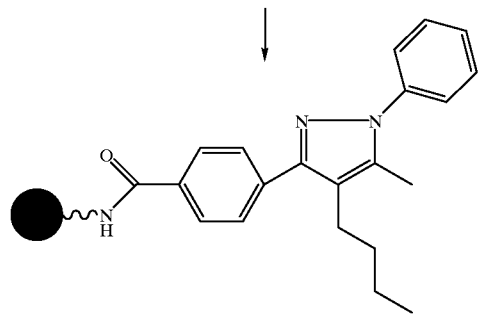

9

Example 17
Synthesis of Fused Pyrazole and Pyran Rings

Compound III was prepared as follows. Synthesis of a solid support-bound pyrazolidinone is shown below. 100 mg of solid support-bound β-keto ester 13 was suspended in 1 mL of dry DMSO and 50 μL phenylhydrazine. The reaction vessel was heated to 70° C. with constant agitation for 18 hrs to produce pyrazolidinone 16 (general structure). The cooled, derivatized solid support was then filtered and washed with dimethylformamide and dichloromethane. 70 mg of pyrazolidinone I was suspended in toluene (1 mL). Piperidine (70 μL equivalent to 700 μmol), benzaldehyde (144 μL equivalent to 1400 μmol) and 4 A° molecular sieves (1 spatula tip) were added and the reaction mixture was agitated at room temperature. After decanting from the sieves, the solid support was washed with dichloromethane six times. The resultant product, solid support-bound compound II, was suspended in DMSO (1 mL). Piperidine (70 μL equivalent to 700 μmol) and malononitrile (93 mg, equivalent to 1400 μmol) were added and the reaction mixture was briefly sparged with argon and then heated (60–120° C.). After cooling, the reaction mixture is drained and washed with dichloromethane (six times), methanol (three times) and dichloromethane (three times). The solid support was treated with 20% trifluoroacetic acid in dichloromethane for 20 minutes, filtered, and volatiles evaporated under a stream of argon to provide compound III.

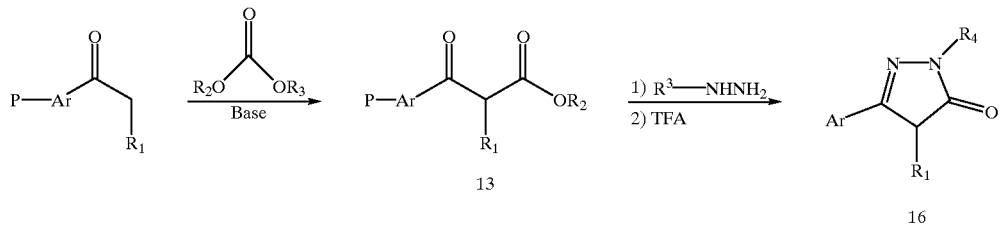

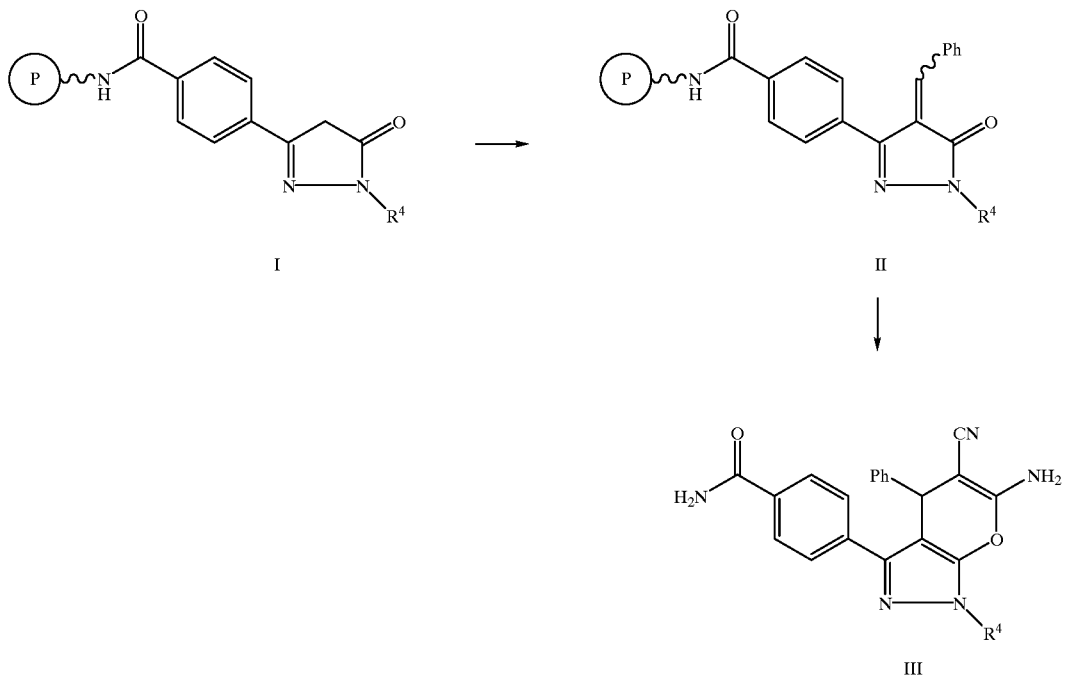

Another pyrazole synthesis:

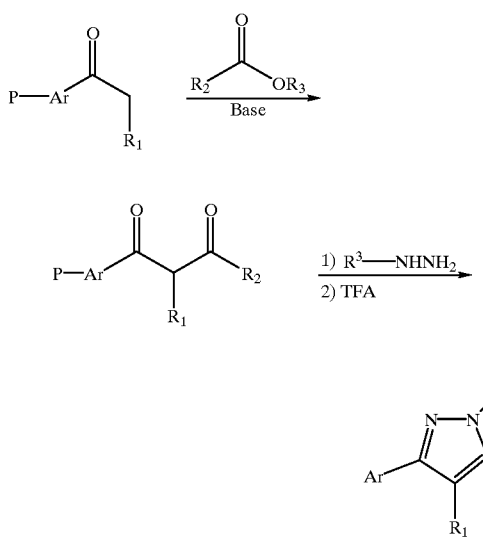

Example 18
Synthesis of a 2-amino-pyrimidine

Preparation of compound 6 was performed as follows. 75 mg of solid support-bound compound 2 (35 μmol) was suspended in 750 μL dry DMSO with 67 mg of guanidine hydrochloride (700 μmol). The hydrochloride salt was then neutralized in situ with 500 μL of 1M potassium tert-butoxide (500 μmol) in kTHF under a stream of argon. The reaction vessel was then heated to 70° C. with constant agitation for 18 hrs. The cooled, derivatized solid support was then filtered and washed with dimethylformamide, water, dimethylformamide, and dichloromethane. The solid support was treated with 20% trifluoroacetic acid in dichloromethane for 20 minutes, filtered, and volatiles evaporated under a stream of argon to produce compound 6 detached from the solid support. An electrospray MS peak of 229 (M+1) was consistant with the structure of 6 detached from the solid support.

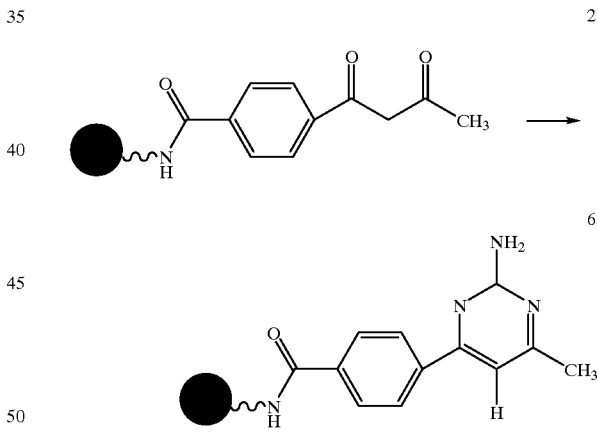

Example 19
Synthesis of Chalcone 3

To a mixture of 50 mg (0.47 mmol) benzaldehyde and 100 mg (0.047 mmol) Rink amide resin bound compound 1 in 5 mL THF, 12 μL 2M sodium ethoxide was added. It was shaken at room temperature for 2 hours. The resulting Resin bound compound 2 was collected in a 3 mL filtering column and washed with water (3×2 mL), DMF (2×2 mL) and methylene chloride (3×2 mL). After drying under vacuum, 5 mg Resin bound compound 2 was treated with 1.5 mL 5% trifluoroacetic acid in methylene chloride for 20 minutes. The solid was filtered off and washed with 1 mL methylene chloride, combined methylene chloride solution was concentrated and dried under vacuum to give 0.5 mg product 3. MS m/z252 (M⁺+1).

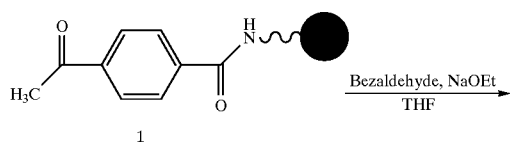

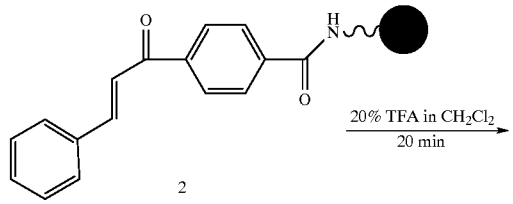

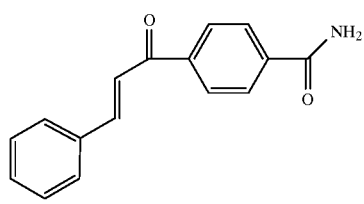

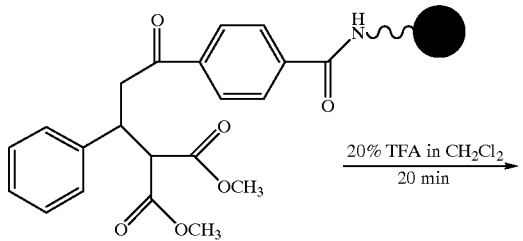

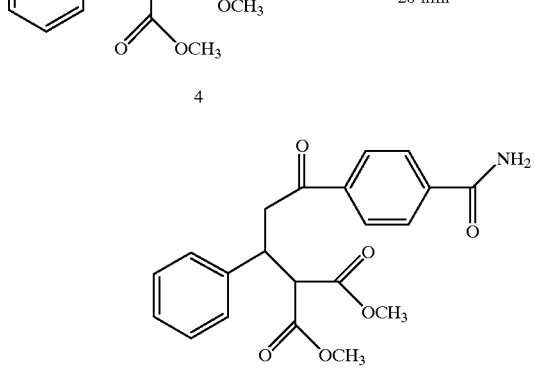

Example 20
Synthesis of Diester 5

To a mixture of 20 mg (0.009 mmol) Rink resin bound compound 2 and 25 mg (0.18 mmol) dimethyl malonate in 0.60 mL THF, 13 μL 1,8-diazabicyclo[5.4.0] undec-7-ene (0.09 mmol) was added. It was shaken at 40° C. under argon for 2 hours. The resulting Rink Resin bound bond compound 4 was collected in a 3 mL filtering column and washed with DMF (2×2 mL), $CH_2Cl_2$ (2×2 mL). After drying under vacuum, 5 mg Resin bound compound 4 was treated with 1 mL $CH_2Cl_2$, combined $CH_2Cl_2$ solution was concentrated under vacuum to give 0.8 mg product 5. MS m/z 384 ($M^+ +1$).

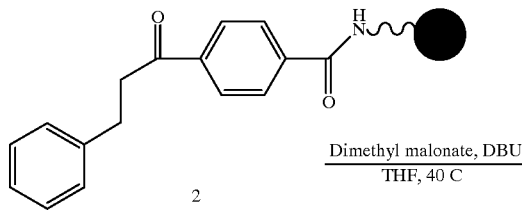

Example 21

Synthesis Tetrahydropyridone 9

To a mixture of 10 mg (0.0047 mmol) Rink Amide Resin bounded compound 4 and 7 mg (0.047 mmol) 4-methoxybenzylamine and 0.8 mL 1M $NaBH_3CN$ in THF, 1 drop acetic acid and 1 drop $H_2O$ were added. The mixture was sealed under argon and shaken at 75° C. for 24 hours. The final Resin bounded compound 8 was washed with DMF (3×2 mL), $H_2O$ (2×2 mL) and $CH_2Cl_2$ (3×2 mL). It was treated with 5% trifluoroacetic acid in $CH_2Cl_2$ for 20 minutes. The solid was filtered off and washed with 1 mL $CH_2Cl_2$, combined $CH_2Cl_2$ solution was concentrated under vacuum to give 1.8 mg product 9. MS m/z 469 ($M_+ +1$).

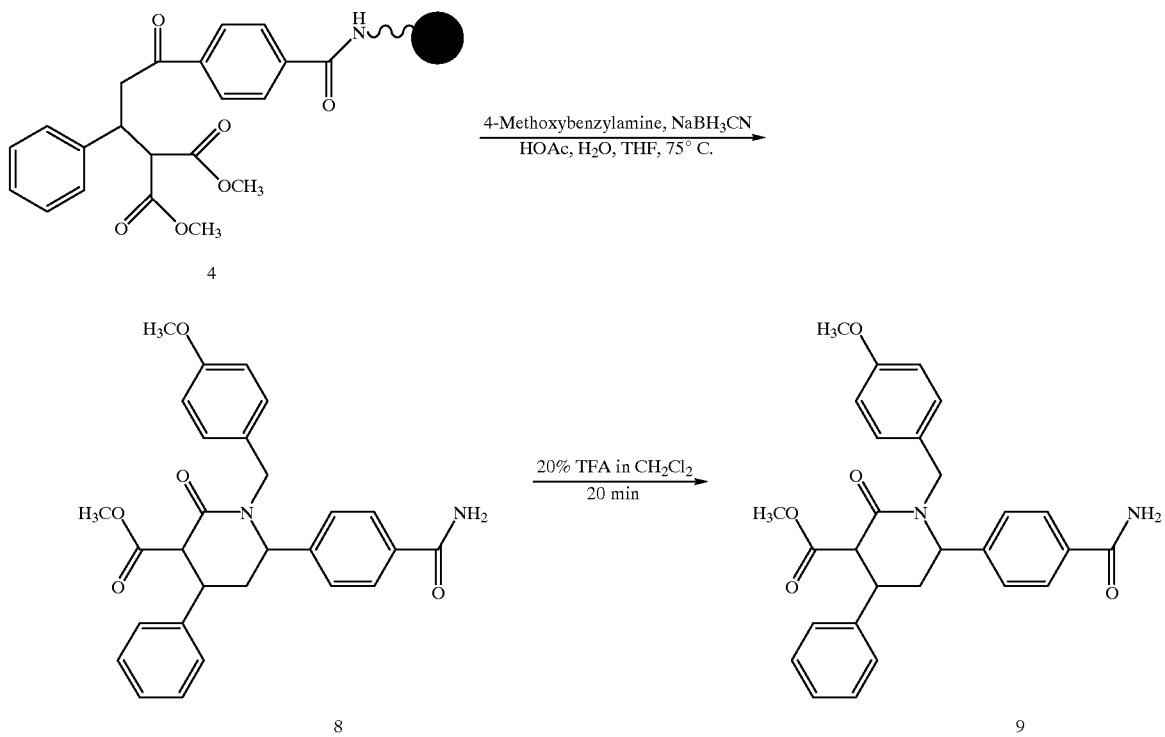

Example 22
Synthesis of Dihydropyridone 7

To a mixture of 10 mg (0.0047 mmol) Rink Amide Resin bounded compound 4 and 7 mg (0.047 mmol) 4-methoxybenzylamine in 0.8 mL toluene, 1 drop acetic acid was added. The mixture was sealed under argon and shaken at 80° C. for 15 hours. The final Resin bounded compound 6 was washed with DMF (3×2 mL), $H_2O$ (2×2 mL) and $CH_2Cl_2$ (3×2 mL). It was treated with 5% trifluoroacetic acid in $CH_2Cl_2$ solution was concentrated under vacuum to give 1.8 mg product 7. MS m/z 471 ($M^+$+1).

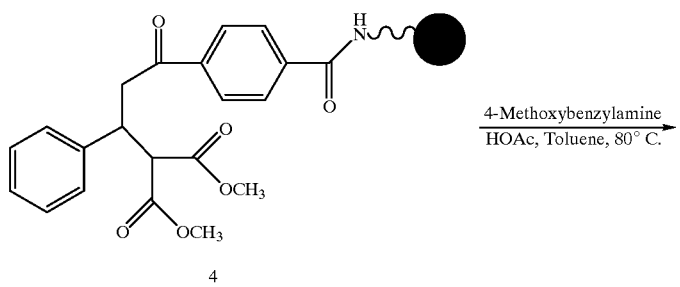

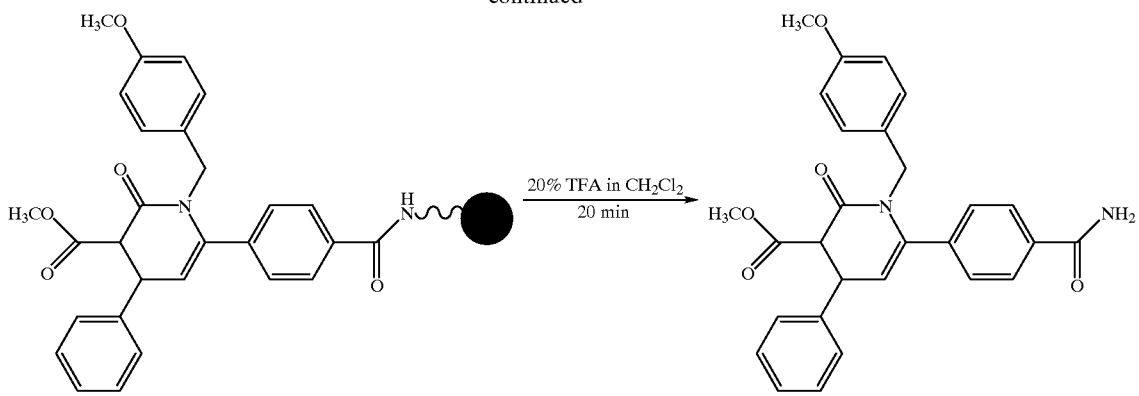

Example 23

The resin 1 (100 mg, 0.056 mmol) was combined in 1.5 ml off a 1:1 mixture of EtOH and 1,4-dioxane followed by the addition of 130 μl (1.12 mmol) acetophenone and 87 mg (1.12 mmol) NH₄OAc. The reaction mixture was shaken overnight at 80–85° C. and washed with H₂O, MsOH, and CH₂Cl₂. The resin 2 was cleaved with 10% TFA in CH₂Cl₂ to give the 3. ESMS m/z=351 (M+1). The resin 4 was treated with the same reaction conditions to give the pyridine 6. ESMS m/z=315 (M+1).

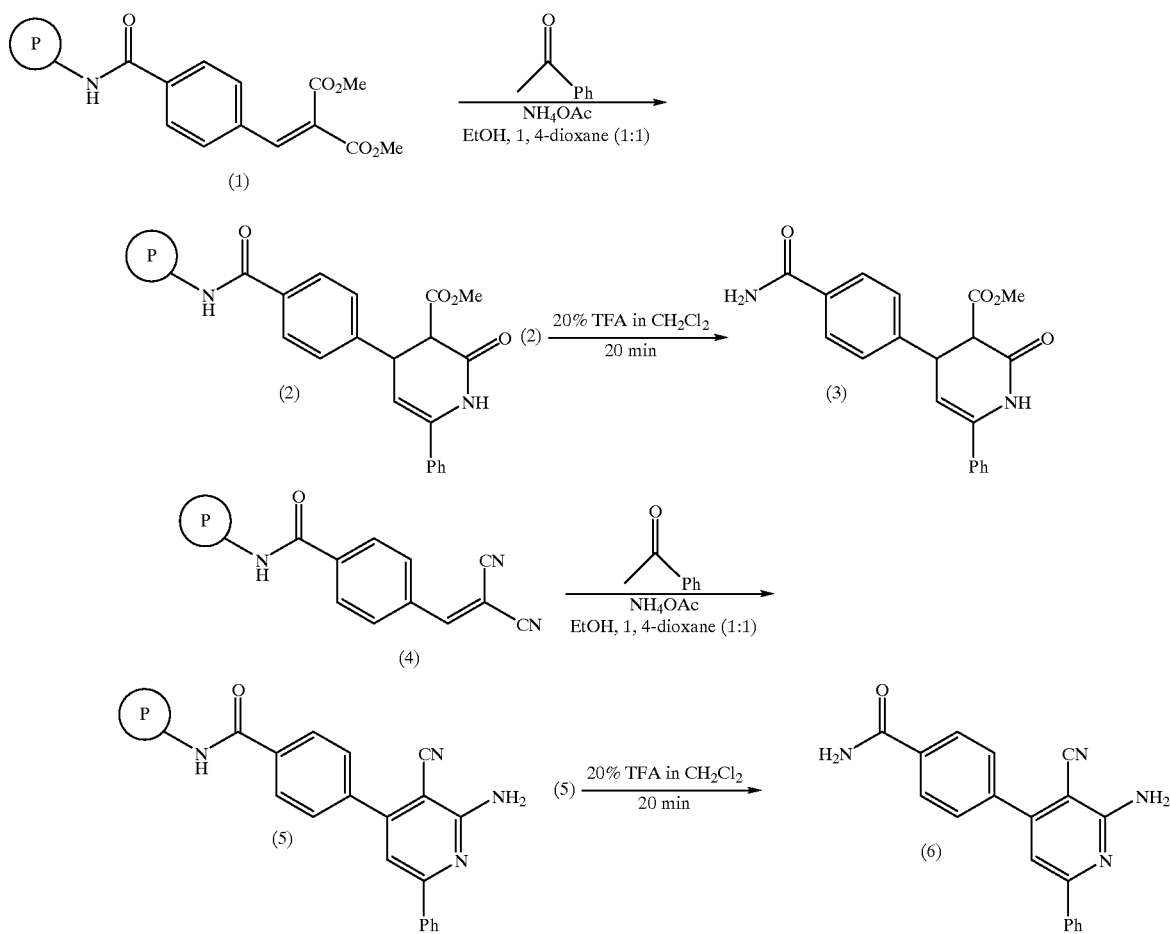

Example 24
Synthesis of Isoxazole

To a solution of 44 mg (0.11 mmol) a D-glucopyranosylnitromethane tetra-acetate (alpha anomer)

and 24 μL (0.22 mmol) phenyl isocyanate in 0.80 mL 1,2-dichloroethane containing 30 mg (0.016 mmol) Rink Amide Resin bound compound 1, 2 mL (0.016 mmol) triethylamine was added under argon. The mixture was refluxed and shaken at 78° C. for 15 hours. It was allowed to cool down to room temperature. The resin bound compound 2 was collected in a 3 mL filtering column and was washed with N,N-dimethylformamide (3×2 mL), methylene chloride (3×2 mL) and dried under vacuum. The dried Resin bound compound 2 was treated with 2 mL 20% trifluoroacetic acid in methylenechloride for 20 minutes. The solid was filtered off and washed 3 times with 1.5 mL methylene chloride. The combined washings were concentrated and dried under vacuum to give 12 mg product 3 of ca. 95% purity. The spectral data consisted of: Electrospray MS m/z 884 (M$^+$+1).

Example 24

Synthesis of Substituted Pyran

Compound 18, a 2-amino-3-cyano pyran, was prepared by the following procedure. Prep. of a,b unsat-ketone from ketone: P—Ar—C(O)—CH2—R. At this point the split resin method adds diversity as well as in the next step of cyclization. A substituted α,β-unsaturated ketone covalently attached to solid support resin (47 μmol) was suspended in SOLVENT (1 mL). Dicyanomethane was added and the reaction mixture was agitated. After cooling, the derivatized solid support was washed with dichloromethane (six times), methanol (three times), and dichloromethane (three times). The solid support was treated with 20% trifluoroacetic acid in dichloromethane for 20 minutes, filtered, and volatiles evaporated under a stream of argon to provide product 18 cleaved from the solid support.

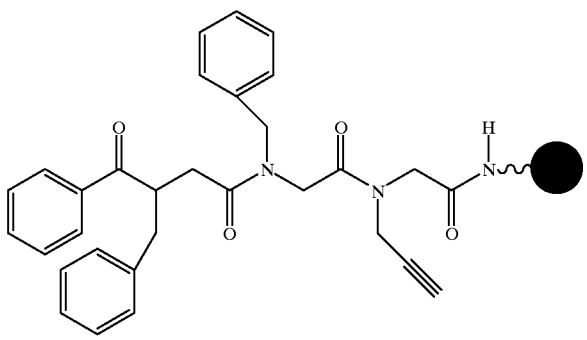

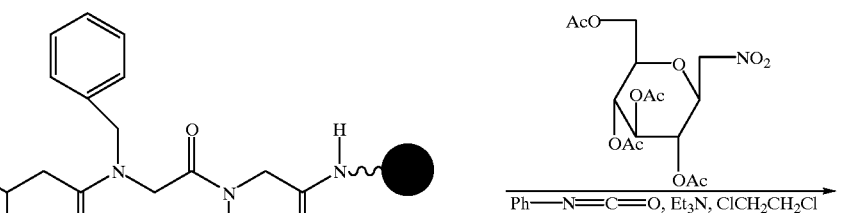

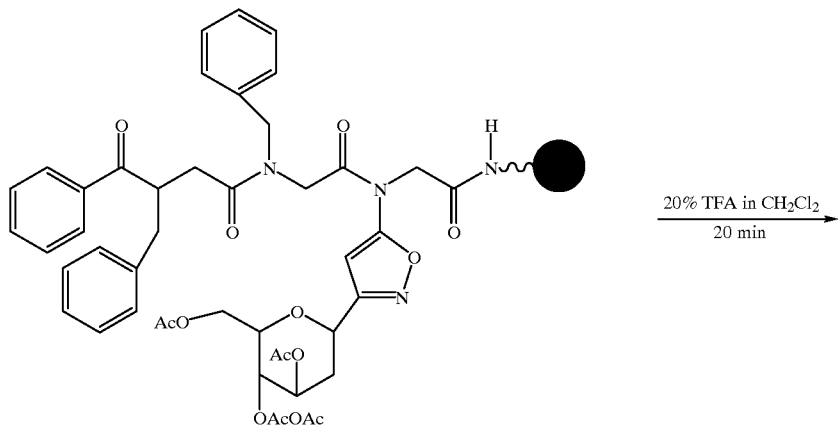

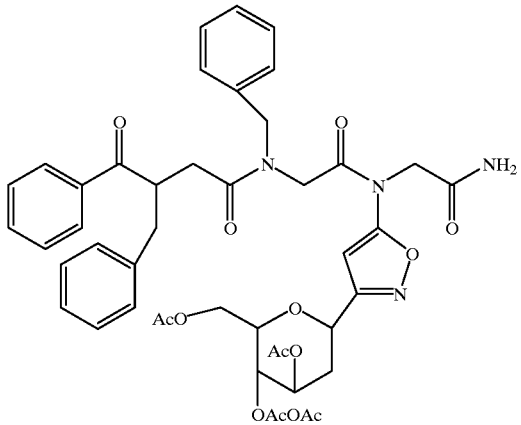

A mixture of compounds 18 are synthesized by first preparing a mixture of α,β-unsaturated ketones on solid support resin. The diversity of the mixture is controlled by the variety of R groups of the α,β-unsaturated ketone. Each of the R groups can independently be an alkyl or aryl. Further, the β,β-unsaturated ketone can be covalently attached to the resin at any one of the R group positions. The mixture of solid support bound ketones is then reacted with DI-CYANO METHANE as described above to produce a mixture of compounds having the general structure, 18.

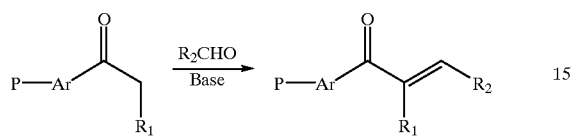

General synthesis of α,βunsaturated ketone.

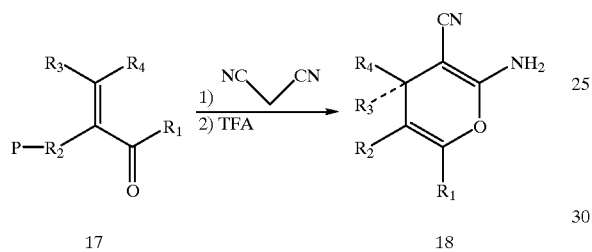

Example 26

Synthesis of Piperadine-2-ones

Piperadine-2-ones having the general structure of compound 4 were prepared by the following procedure. A solid support-bound α,β-unsaturated ketone such as compound 2 was suspended in SOLVENT (1 mL). yy μmol of ester S' is added and the reaction mixture is agitated at suitable temperature for a sufficient amount of time to produce solid support-bound compound T. The derivatized solid support is washed with dicloromethane (six times) and filtered. At this point the solid support may be split into portions for the different reactions producing compounds 4 and 5.

Compound U is produced by suspending xx μmol of solid support-bound compound 3 in SOLVENT (1 mL). A primary amine and NaBH3CN are added and the reaction mixture is agitated at a suitable temperature for an appropriate amount of time. After cooling, the derivatized solid support was washed with dichloromethane (six times), methanol (three times), and dichloromethane (three times). The solid support was treated with 20% trifluoroacetic acid in dichloromethane for 20 minutes, filtered, and volatiles evaporated under a stream of argon to provide product 4 cleaved from the solid support. A mixture of compounds having the general structure of 4 are prepared by varying the R groups. R1, R2, R3, and R4 are independently any alkyl, aromatic, heteroaromatic group or hydrogen. Ar is any aromatic or heteroaromatic moiety. X is any aromatic or heteroaromatic moiety or an electron withdrawing group.

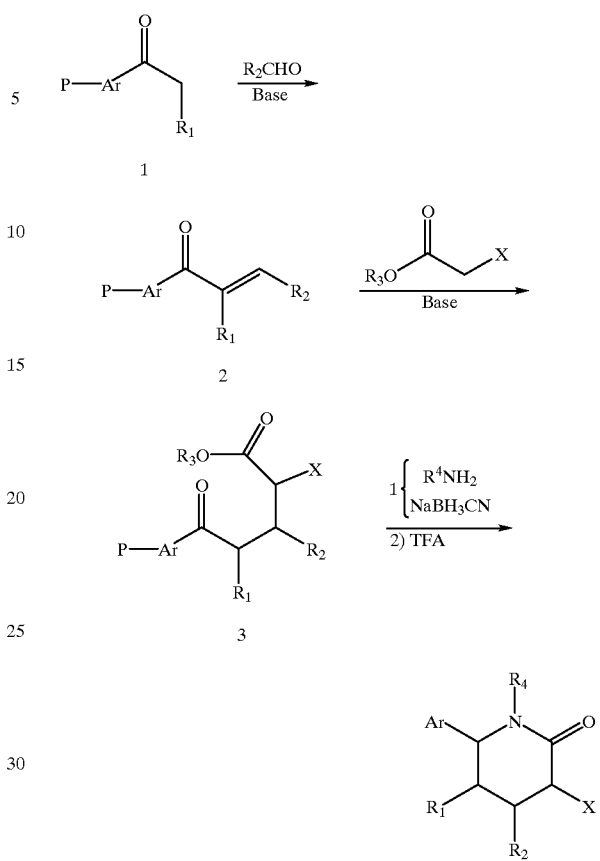

$R_1$, $R_2$, $R_3$, $R_4$=H, alkyl, aromatic, heteroaromatic

Ar=aromatic or heteroaromatic

X=Ar or EWG

Example 27

Synthesis of tetrahydropyradine-2-one

Compound 5 is produced by suspending solid support-bound compound 3 in SOLVENT (1 mL) containing acetic acid. A primary amine is added and the reaction mixture is agitated at a suitable temperature for an appropriate amount of time. After cooling, the derivatized solid support was washed with dichloromethane (six times), methanol (three times), and dichloromethane (three times). The solid support was treated with 20% trifluoroacetic acid in dichloromethane for 20 minutes, filtered, and volatiles evaporated under a stream of argon to provide product 5, a tetrahydro-2-pyridone, cleaved from the solid support. A mixture of compounds having the general structure of 5 are prepared by varying the R groups on the submonomers. R1, R2, R3, and R4 are independently any alkyl, aromatic, heteroaromatic group or hydrogen. Ar is any aromatic or heteroaromatic moiety. X is any aromatic or heteroaromatic moiety or an electron withdrawing group as defined herein.

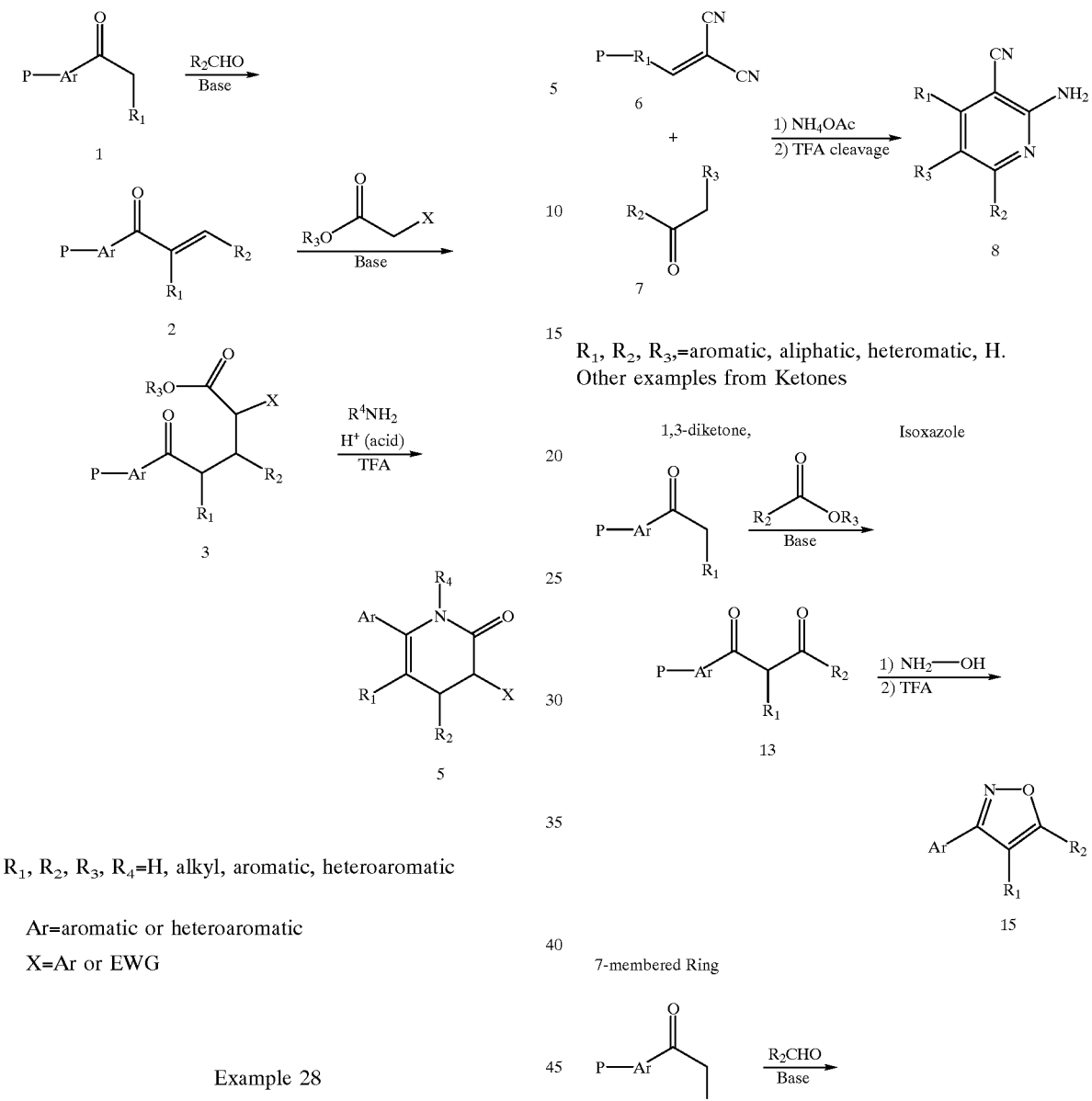

$R_1$, $R_2$, $R_3$, $R_4$=H, alkyl, aromatic, heteroaromatic

Ar=aromatic or heteroaromatic

X=Ar or EWG

Example 28

Synthesis of Substituted Pyridines

Compound 8, a 2-amino-3-cyano-pyridine, was prepared as follows. Solid support-bound compound 6 was suspended in SOLVENT (1 mL) with ammonium acetate. Ketone 7 was added and the reaction mixture was agitated at a suitable temperature for an appropriate amount of time. After cooling, the derivatized solid support was washed with dichloromethane (six times), methanol (three times), and dichloromethane (three times). The solid support was treated with 20% trifluoroacetic acid in dichloromethane for 20 minutes, filtered, and volatiles evaporated under a stream of argon to provide product 8, a 2-amino-3-cyano-pyridine, cleaved from the solid support. A mixture of compounds having the general structure of 8 are prepared by varying the R groups of the submonomer starting materials. R1, R2, and R3 are independently any alkyl, aromatic, heteroaromatic group or hydrogen.

$R_1$, $R_2$, $R_3$,=aromatic, aliphatic, heteromatic, H. Other examples from Ketones

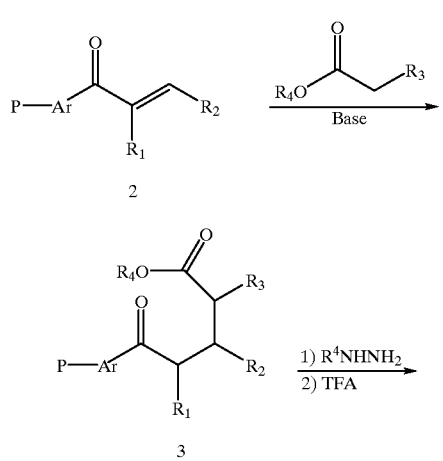

-continued

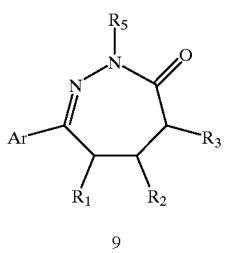

9

$R_1, R_2, R_3, R_4$=H, alkyl, aromatic, heteroaromatic
  Ar=aromatic or heteroaromatic
  X=Ar or EWG

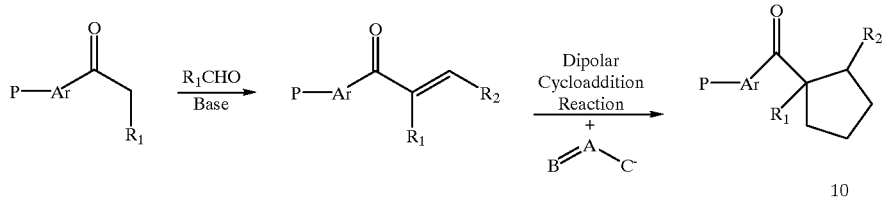

10

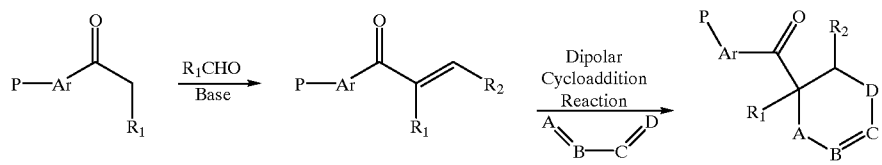

11

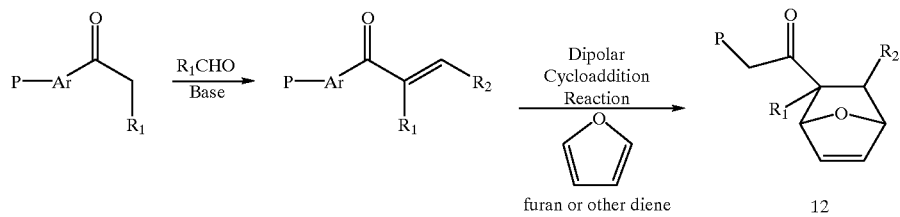

12

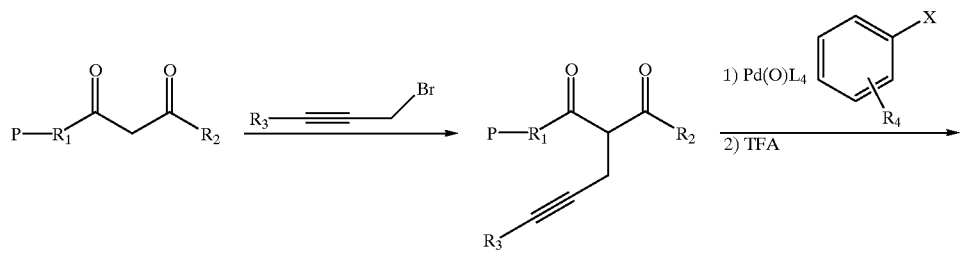

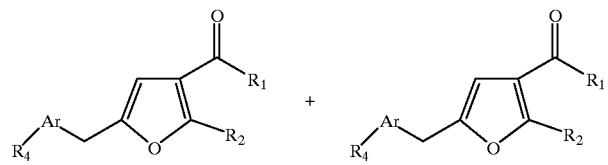

While the present invention has been described with reference to the specific embodiments thereof, it should be understood by those skilled in the art that various changes may be made and equivalents may be substituted without departing from the true spirit and scope of the invention. In addition, many modifications may be made to adapt a particular reaction, material, library, process, process step or steps, to the objective, spirit and scope of the present invention. All such modifications are intended to be within the scope of the claims appended hereto.

What is claimed is:

1. A method of synthesizing a library of substrate bound cyclic organic compounds, said method comprising:

(a) providing a plurality of solid support surfaces;

(b) derivatizing each of the surfaces with XII, wherein X is selected from the group consisting of O and NH to provide a plurality of derivatized support surfaces as follows:

P—XH where "P" is one of the support surfaces;

(c) dividing the derivatized support surfaces into a plurality of subamounts;

(d) reacting a different submonomer of the following general structural formula with the —XH group of each subamount of derivatized support surface

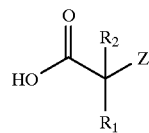

wherein $R_1$ and $R_2$ are independently any sidechain moiety covalently attachable to the carbon atom and Z is a halogen and driving each reaction to completion to obtain

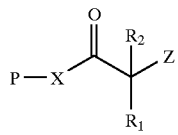

(e) recombining each subamount and mixing to obtain a mixture of solid supports with a plurality of different compounds thereon;

(f) dividing the mixture into a plurality of subamounts;

(g) reacting a different cyclic compound of the following general structural formula with the —Z moiety of each subamounts

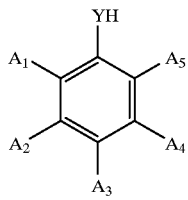

wherein Y is selected from the group consisting of —O— and —S—, and each of $A_1$, $A_2$, $A_3$, $A_4$ and $A_5$ is independently a moiety selected front the group consisting of H, a hydrocarbyl, a ketone, an aldehyde, a carboxylic acid, an ester, amide, an amine, a nitrile and an ether to obtain a compound of the following structure:

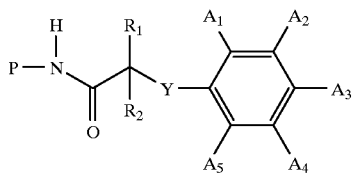

and;

(h) recombining the subamounts to provide a library of cyclic organic compounds on a plurality of solid support surfaces.

2. The method of claim 1, wherein Z is Br.

3. The method of claim 1, wherein $R_1$ and $R_2$ are each independently H or a hydrocarbyl.

4. The method of claim 1, wherein each of $A_1$, $A_2$, $A_3$, $A_4$, and $A_5$ is independently H or hydrocarbyl.

5. The method of claim 1, wherein each of $R_1$, $R_2$, $A_1$, $A_2$, $A_3$, $A_4$, and $A_5$ is independently selected from the group consisting of H, hydroxy, $R_a$, —$OR_a$, —$NR_aR_b$,

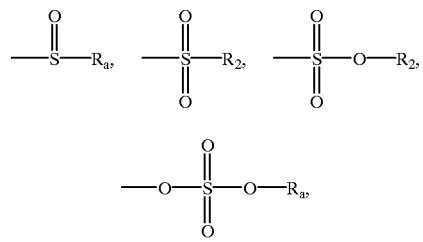

—C(O)$R_a$, —C(O)O$R_a$, —OC(O)$R_a$, —OC(O)O$R_a$, —N$R_b$C(O)$R_a$, —C(O)N$R_aR_b$, —OC(O)N$R_aR_b$, —N$R_c$C(O)N$R_aR_b$, —N$R_b$C(O)O$R_a$, —$R_a$—O—$R_b$, —$R_a$—N$R_bR_c$, —$R_a$—S—$R_b$, —$R_a$—S(O)—$R_b$, —$R_a$—S(O)$_2$—$R_b$, —O$R_a$—O—$R_b$, —N$R_aR_b$—O—$R_c$,

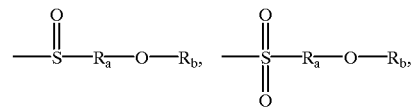

—C(O)$R_a$—O—$R_b$, —C(O)O$R_a$—O—$R_b$, —OC(O)$R_a$—O—$R_b$, —OC(O)O$R_a$—O—$R_b$, —N$R_b$C(O)$R_a$—O—$R_c$, —C(O)N$R_aR_b$—O—$R_c$, —OC(O)N$R_aR_b$—O—$R_c$, —N$R_c$C(O)N$R_aR_b$—O—$R_d$, —N$R_b$C(O)O$R_a$—O—$R_c$, —O$R_a$—S—$R_b$, —N$R_aR_b$—S—$R_c$,

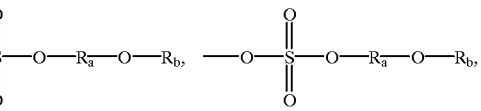

—C(O)$R_a$—S—$R_b$, —C(O)O$R_a$—S—$R_b$, —OC(O)$R_a$—S—$R_b$, —OC(O)O$R_a$—S—$R_b$, —N$R_b$C(O)$R_a$—S—$R_c$, —C(O)N$R_aR_b$—S—$R_c$, —OC(O)N$R_aR_b$—S—$R_c$, —N$R_c$C(O)N$R_aR_b$—S—$R_d$, —N$R_b$C(O)O$R_a$—S—$R_c$, —O$R_a$—N$R_bR_d$, —N$R_aR_b$—N$R_cR_d$,

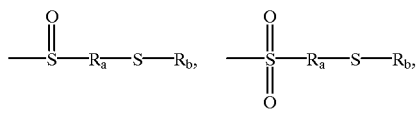

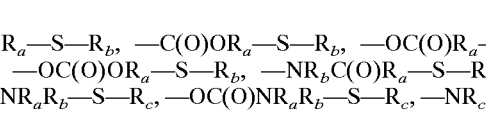

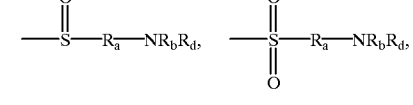

—C(O)$R_a$—N$R_bR_d$, —C(O)O$R_a$—N$R_bR_d$, —OC(O)$R_a$—N—$R_bR_d$, —OC(O)O$R_a$—N$R_bR_d$, —N$R_b$C(O)$R_a$—N$R_cR_d$, —C(O)N$R_aR_b$—N$R_cR_d$, —OC(O)N$R_aR_b$—N$R_cR_d$, —N$R_c$C(O)N$R_aR_b$—NH$R_d$, —N$R_b$C(O)O$R_a$—N$R_cR_d$;

where $R_a$, $R_b$, $R_c$ and $R_d$ are each independently alkyl, alkenyl, aryl, aralkyl, aralkenyl or aralkynyl of 1 to 12 carbon atoms;

where $R_a$, $R_b$, $R_c$ and $R_d$ are each substituted with 0–6 halo, $NO_2$, —OH, lower alkyl, —SH, —$SO_3$, —$NH_2$, lower acyl, lower acyloxy, lower alkylamino, lower dialkylamino, trihalomethyl, —CN, lower alkylthio, lower alkylsufinyl, or lower alkylsulfonyl wherein "lower" indicates 1 to 6 carbon atoms.

6. The method of claim 1, wherein each of $R_1$, $R_2$, $A_1$, $A_2$, $A_3$, $A_4$, and $A_5$ is independently selected from the group consisting of H, an alkyl containing 1 to 6 carbon atoms and one of the twenty naturally occurring amino acids.

7. The method of claim 1, wherein at each dividing step the division is into 3 or more subamounts.

8. The method of claim 1, wherein at each dividing step the di vision is into 10 or more subamounts.

9. The method of claim 1, wherein at each dividing step the division is into 20 or more subamounts.

10. A library of compounds produced by the method as claimed in claim 1.

11. The method of claim 1, further comprising cleaving the compounds from the solid support surfaces.

12. The library produced by the method of claim 11.

13. A method of determining the biological activity of a compound, comprising:

providing the library of claim 12;

contacting the library with a biological receptor; and determining a compound in the library with activity with respect to the receptor.

14. The method of claim 13, wherein the receptor is bound to a solid support.

* * * * *

UNITED STATES PATENT AND TRADEMARK OFFICE
CERTIFICATE OF CORRECTION

PATENT NO. : 5,958,792
DATED : September 28, 1999
INVENTOR(S) : Manoj C. Desai et al.

It is certified that error appears in the above-identified patent and that said Letters Patent is hereby corrected as shown below:

On the title page, item 75, Inventors: delete "Manoi" and replace it with --Manoj--

In the Specification:

Column 52, line 10, delete "XII" and insert --XH--
Column 53, line 50, delete graphic and insert the following:

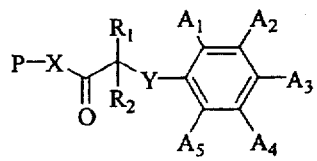

Column 55, line 17, delete "di vision" and insert --division--

Signed and Sealed this

Sixth Day of June, 2000

Attest:

Q. TODD DICKINSON

Attesting Officer          Director of Patents and Trademarks